(12) United States Patent
Gao et al.

(10) Patent No.: US 8,471,021 B2
(45) Date of Patent: Jun. 25, 2013

(54) SULFUR CONTAINING HETEROCYCLE-FUSED NAPHTHALENE TETRACARBOXYLIC ACID DIIMIDE DERIVATIVES, PREPARATION METHOD AND USE THEREOF

(75) Inventors: Xike Gao, Shanghai (CN); Chong-an Di, Beijing (CN); Daoben Zhu, Beijing (CN); Yunqi Liu, Beijing (CN); Hongxiang Li, Shanghai (CN); Biao Jiang, Shanghai (CN)

(73) Assignees: Shanghai Institute Of Organic Chemistry, Chinese Academy Of Sciences (CN); Institute Of Chemistry, Chinese Academy Of Sciences (CN)

( * ) Notice: Subject to any disclaimer, the term of this patent is extended or adjusted under 35 U.S.C. 154(b) by 0 days.

(21) Appl. No.: 13/453,668

(22) Filed: Apr. 23, 2012

(65) Prior Publication Data

US 2012/0253045 A1 Oct. 4, 2012

Related U.S. Application Data

(63) Continuation of application No. PCT/CN2010/077932, filed on Oct. 21, 2010.

(30) Foreign Application Priority Data

Oct. 23, 2009 (CN) .......................... 2009 1 0197611
Jun. 23, 2010 (CN) .......................... 2010 1 0207565

(51) Int. Cl.
C07D 495/22 (2006.01)
H01L 51/00 (2006.01)
H01L 29/00 (2006.01)

(52) U.S. Cl.
USPC ............................... 546/41; 313/504; 257/40

(58) Field of Classification Search
USPC ................................. 546/41; 313/504; 257/40
See application file for complete search history.

(56) References Cited

U.S. PATENT DOCUMENTS 2,361,524 A 10/1944 Allardt et al.

FOREIGN PATENT DOCUMENTS

| CN | 1526702 A | 9/2004 |
| CN | 101550104 A | 10/2009 |
| CN | 101693719 A | 4/2010 |

OTHER PUBLICATIONS

Gao, X. et al.: Core-expanded Naphthalene diimides fused with 2-(1,3-dithiol-2-Ylidene)malonitrile groups for high performance, ambient-stable, solution-processed n-channel organic thin film transistors. J. Am. Chem. Soc., vol. 132, pp. 3697-3699, 2010.*

Yan, H. et al.; "A High-Mobility Electron-Transporting Polymer for Printed Transistors"; Nature. 2009, 457, 679-686.

Thompson, M. E. ed. Chem. Rev. 2007, 107, 923-925.

Korzhov, M. et al.; "Dreaming in Plastic"; Physics Word. 2008, 29-33.

Liang, Y. et al.; "For the Bright Future—Bulk Heterojunction Polymer Solar Cells with Power Conversion Efficency of 7.4%"; Adv. Mater. 2010, 22, E135-E138.

Osaka, I. et al.; "High—Mobility Semiconducting Naphthodithiophene Copolymers"; J. Am. Chem. Soc. 2010, 132, 5000-5001.

Ebata, H. et al.; "Highly Soluble [1] Benzothieno[3,2-b]benzothiophene (BTBT) Derivatives for High-Performance, Solution-Processed Organic Field-Effect Transistors"; J. Am. Chem. Soc. 2007, 129, 15732-15733.

(Continued)

*Primary Examiner* — Charanjit Aulakh
(74) *Attorney, Agent, or Firm* — St. Onge Steward Johnston & Reens LLC

(57) ABSTRACT

Sulfur containing heterocycle-fused naphthalenetetracarboxylic acid diimide derivatives represented by formula (I) are disclosed,

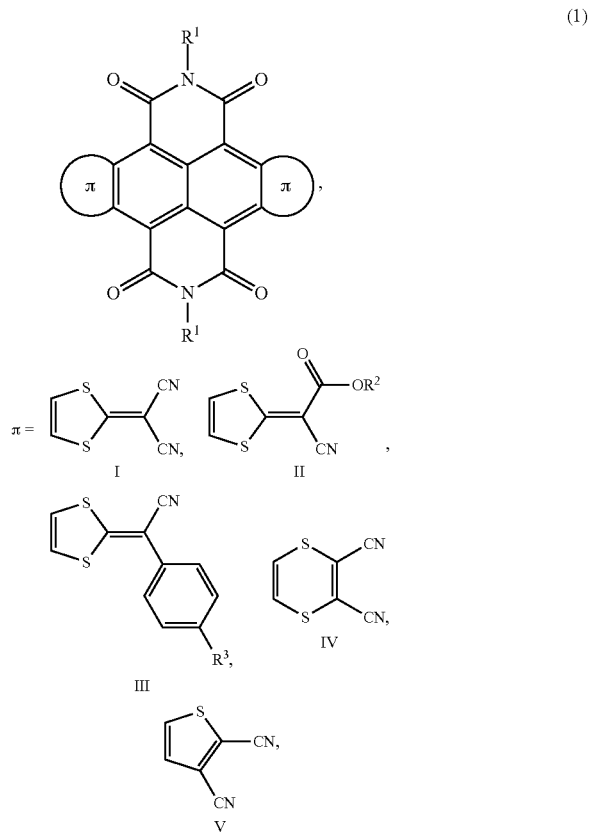

in which, $R^1$ and $R^2$ are $C_1$-$C_{30}$ and $C_1$-$C_{12}$ linear alkyl or branched alkyl, respectively; $R^3$ is H or halogen atom. The preparation method of the derivatives and the use thereof in manufacture of organic thin film field effect transistor or organic solar batteries are also disclosed.

13 Claims, 9 Drawing Sheets

OTHER PUBLICATIONS

Newman, C. R. et al.; "Introduction of Organic Thin Film Transistors and Design of n-Channel Organic Semiconductors"; Chem. Mater. 2004, 16, 4436-4451.

International Preliminary Report on Patentability & Written Opinion of the International Searching Authority; Application No. PCT/CN2010/077932; Issued: Apr. 24, 2012; 7 pages.

International Search Report; Application No. PCT/CN2010/077932; Issued: Jan. 6, 2011; Mailing Date: Feb. 10, 2011; 5 pages.

McCulloch, I. et al.; "Liquid-Crystalline Semiconducting Polymers with High Charge-Carrier Mobility"; Nat. Mater. 2006, 5, 328-333.

Odobel, F. et al.; "New Photovoltaic Devices Based on the Sensitization of p-type Semiconductors: Challenges and Opportunities"; Acc. Chem. Res. 2010, 43, 1063-1071.

Leenen, M. A. M. et al.; "Printable Electronics: Flexibility for the Future"; Phys. Status Solidi A. 2009, 206, 588-597.

Forrest, S. R.; "The path to ubiquitous and low-cost organic electronic appliances on plastic"; Nature. 2004, 428, 911-918.

Klauk, H. et al.; "Ultralow-Power Organic Complementary Circuits"; Nature. 2007, 445, 745-748.

Ko, et al.; "Various Digital Memory Behaviors of Functional Aromatic Polyimides Based on Electron Donor and Acceptor Substituted Trihenylamines"; American Chemical Society—Macromolecules; Feb. 14, 2012; pp. A-J.

* cited by examiner

# SULFUR CONTAINING HETEROCYCLE-FUSED NAPHTHALENE TETRACARBOXYLIC ACID DIIMIDE DERIVATIVES, PREPARATION METHOD AND USE THEREOF

CROSS-REFERENCE TO RELATED APPLICATIONS

The present application is a continuation of pending International patent application PCT/CN2010/077932, filed on Oct. 21, 2010, which designates the United States and claims priority from Chinese patent application 201010207565.9, filed on Jun. 23, 2010, and Chinese patent application 200910197611.9, filed on Oct. 23, 2009. The content of all prior applications is incorporated herein by reference.

FIELD OF THE INVENTION

The present invention relates to organic semiconductors, which are sulfur-containing heterocycle-fused naphthalenetetracarboxylic acid diimides, and particularly, relates to 5 classes of sulfur containing heterocycle-fused naphthalenetetracarboxylic acid diimide derivatives, and preparation thereof, and their applications as n-type organic semiconductors in organic thin-film transistors, etc.

BACKGROUND OF THE INVENTION

In comparison with inorganic semiconductors such as silicon, oxide and the like, organic semiconductors are easier to fabricate, cheaper, lighter, more flexible, and more compatible with plastic substrates, therefore, they have broad applications in flexible displays, organic radio frequency identification (ORFID), organic sensors, organic solar cells, etc. (Forrest, S. R. *Nature.* 2004, 428, 911-918; Korzhov, M. et al. *Physics Word.* 2008, 29-33; Leenen, M. A. M. et al. *Phys. Status Solidi A.* 2009, 206, 588-597; Special issue: Organic Electronics and Optoelectronics, Forrest, S. R.; Thompson, M. E. ed. *Chem. Rev.* 2007, 107, 923-1386 etc.) Along with the development in techniques related to organic semiconductors and devices, thin, portable, flectional, wearable and fashionable organic electronic products will gradually emerge in our daily life, and bring revolutionary transformation to the electronics industry and the life of human beings.

Organic semiconductors, which are the key components of organic electronic devices, can be classified based on their transport carriers into two categories, p-type organic semiconductor/organic donor (hole-transporting), and n-type organic semiconductor/organic acceptor (electron-transporting). In general, the development of p-type organic semiconductor/organic donor is more advanced. The performance of certain organic thin-film transistors (OTFTs) of solution-processable molecular material is comparable to that of amorphous silicon (McCulloch, I. et al. *Nat. Mater.* 2006, 5, 328-333; Ebata, H. et al. *J. Am. Chem. Soc.* 2007, 129, 15732-15733; Osaka, I. et al. *J. Am. Chem. Soc.* 2010, 132, 5000-5001). The photoelectric conversion efficiency of certain D-A structure polymeric donor and organic acceptor (PCBM, a fullerene derivative) constructed heterojunction organic solar cell reaches 7.4% (Liang, Y. et al. *Adv. Mater.* 2010, 22, E135-E138). In the field of OTFTs, n-type organic semiconductors play a critical role in constructing organic p-n junction diodes, ambipolar transistors, and complementary circuits with low power consumption and high noise margin (Newman, C. R. et al. *Chem. Mater.* 2004, 16, 4436-4451; Klauk, H. et al. *Nature.* 2007, 445, 745-748; Yan, H. et al. *Nature.* 2009, 457, 679-686). In the field of organic photovoltaics (OPV), n-type organic semiconductors (organic acceptors) broadly applied in bulk heterojunction organic solar cells are primarily confined within fullerene derivatives (such as PCBM, etc.); organic semiconducting sensitizers used in organic sensitized solar cells are primarily p-type organic semiconductors (Odobel, F. et al. *Acc. Chem. Res.* 2010, 43, 1063-1071). Therefore, the n-type organic semiconductor/organic acceptor, although slowly developing, have becoming the technical bottleneck to the advancing of organic electronics.

Naphthalenetetracarboxylic acid diimide (NDI) is a typical class of n-type organic semiconductors which are widely used in the fabrication of n-type OTFT devices. However, its relatively small conjugated aromatic ring makes it difficult to form an efficient π-π stacking in a solid structure, and the resulting OTFT devices exhibit a relatively low electron mobility; on the other hand, NDI-based OTFT devices fabricated by solution process are quite rare, with the poor film-forming ability and poor device performance. For the seeking of n-type organic semiconductors with high electron mobility, better environmental stability and manufactural easiness, the inventors report five classes of sulfur containing heterocycle-fused naphthalenetetracarboxylic acid diimides (CN200910197611.9, priority date of Oct. 23, 2009; CN201010207565.9, priority date of Jun. 23, 2010): 2-(1,3-dithiacyclopenten-2-ylidene)-2-malononitrile fused naphthalenetetracarboxylic acid diimide derivatives, alkyl 2-(1,3-dithiacyclopenten-2-ylidene)-2-cyanoacetate fused naphthalenetetracarboxylic acid diimide derivatives, 2-(1,3-dithiacyclopenten-2-ylidene)-2-phenyl acetonitrile fused naphthalenetetracarboxylic acid diimide derivatives, 1,4-dithiacyclohexadiene-2,3-dicarbonitrile fused naphthalenetetracarboxylic acid diimide derivatives and α,β-dicyanothiophene fused naphthalenetetracarboxylic acid diimide derivatives, the applications of some such compounds in OTFT devices are also disclosed.

SUMMARY OF THE INVENTION

One objective of the present invention is to provide 5 classes of sulfur containing heterocycle fused naphthalenetetracarboxylic acid diimide derivatives: 2-(1,3-dithiacyclopenten-2-ylidene)-2-malononitrile fused naphthalenetetracarboxylic acid diimide derivatives, alkyl 2-(1,3-dithiacyclopenten-2-ylidene)-2-cyanoacetate fused naphthalenetetracarboxylic acid diimide derivatives, 2-(1,3-dithiacyclopenten-2-ylidene)-2-phenyl acetonitrile fused naphthalenetetracarboxylic acid diimide derivatives, 1,4-dithiacyclohexadiene-2,3-dicarbonitrile fused naphthalenetetracarboxylic acid diimide derivatives and α,β-dicyanothiophene fused naphthalenetetracarboxylic acid diimide derivatives.

Another objective of this invention is to provide the preparation methods of the aforementioned sulfur containing heterocycle fused naphthalenetetracarboxylic acid diimide derivatives.

Still another objective of this invention is to provide the application of the aforementioned sulfur containing heterocycle fused naphthalenetetracarboxylic acid diimide derivatives as n-type organic semiconductors for the construction of OTFT devices.

The present invention relates to five classes of sulfur containing heterocycle fused naphthalenetetracarboxylic acid diimide derivatives, and preparation methods and applications thereof, said derivatives having the structure shown in the formula below:

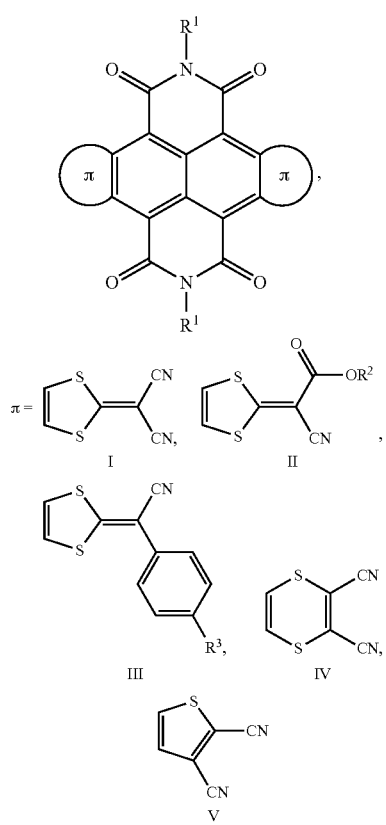

wherein, $R^1$ and $R^2$ are $C_1\sim C_{30}$ and $C_1\sim C_{12}$ n-alkyl or branched alkyl, respectively, $R^1$ is preferably $C_8\sim C_{24}$ n-alkyl or branched alkyl, more preferably $C_{12}\sim C_{24}$ n-alkyl or branched alkyl, further preferably $C_8, C_{12}, C_{14}, C_{16}, C_{17}, C_{20}, C_{24}$ n-alkyl or branched alkyl, specific examples of $R^1$ include, but not limited to, n-octyl, 2-ethylhexyl, 2-butyloctyl, 2-hexyloctyl, 2-hexyldecyl, 3-hexylundecyl, 2-octyldodecyl, 2-decyltetradecyl; $R^2$ is preferably $C_2\sim C_8$ alkyl, more preferably $C_2\sim C_6$ alkyl, specific examples of $R^2$ include, among others, ethyl, n-hexyl, 2-ethylhexyl; $R_3$ is H or halogen atom, preferably H or Br.

Under the protection of inert gas, tetrabromonaphthalene-tetracarboxylic acid diimide reacts with 2,2-dicyanoethylene-1,1-dithiol sodium or alkyl 2-cyanoacetate-ethylene-1,1-dithiol sodium or 2-phenyl acetonitrile (or 4-halo-phenyl acetonitrile)-ethylene-1,1-dithiol sodium to produce 1,3-dithiacyclopentene fused naphthalenetetracarboxylic acid diimide derivatives (I~III); tetrabromonaphthalenetetracarboxylic acid diimide reacts with 1,2-dicyanoethylene-1,2-dithiol sodium to produce 1,4-dithiacyclohexadiene-2,3-dicarbonitrile fused naphthalenetetracarboxylic acid diimide derivatives (IV), and further reacts to produce α,β-dicyanothiophene fused naphthalenetetracarboxylic acid diimide derivatives (V, non separable cis-trans isomers). All these compounds are n-type organic semiconductors. Primary testing result of organic thin-film transistors made by solution process with class I compound as an organic semiconducting layer showed an electron mobility of up to 0.42 cm$^2$/Vs, on/off ratio greater than $10^5$, and a threshold voltage lower than 15 V, both the performance and the environmental stability are better than conventional n-type organic semiconductors.

The advantages of the present invention are:

1. The synthetic process disclosed in the present invention is easy and efficient, starting with materials easily synthesized, costing low during the synthesis, and obtaining target compound with high purity.

2. The sulfur-containing heterocycle fused naphthalenetetracarboxylic acid diimide derivatives have a large π conjugated system and a flexible and soluble friendly alkyl chain. They allow the fabricating of organic electronic devices (such as OTFT, OPV, etc.) using the low-cost solution-based process. Class I compounds are a group of n-type organic semiconductors with excellent device performance and stability. In addition to the applications in n-channel OTFT devices, class II compounds are probably used as a n-type sensitizer in dye sensitized solar cells (coordinating with nickel oxide, etc. when hydrolyzed). Dibromo-substituted class III compounds are hopeful to work as a polymeric monomer along with other donor polymeric units for the construction of D(donor)-A (acceptor) conjugated polymeric semiconductors with narrow band gap and broad band absorption for the application in organic solar cells. Class V compounds, having relatively low LUMO energy level (~4.6 eV), are promising to be used as a p-doping agent in organic-electronics.

DETAILED DESCRIPTION OF THE INVENTION

Figure 1:
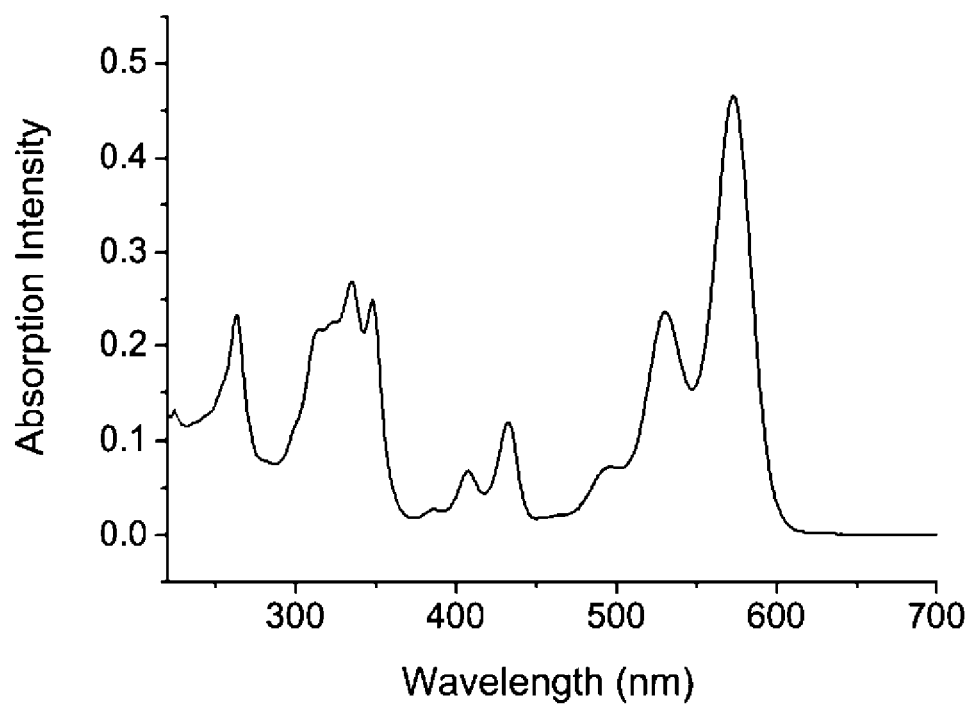
FIG. 1 shows the UV absorption spectrum for compound 1 in dichloromethane.

The present invention provides 5 classes of sulfur containing heterocycle fused naphthalenetetracarboxylic acid diimide derivatives, which are represented by the following general formulae:

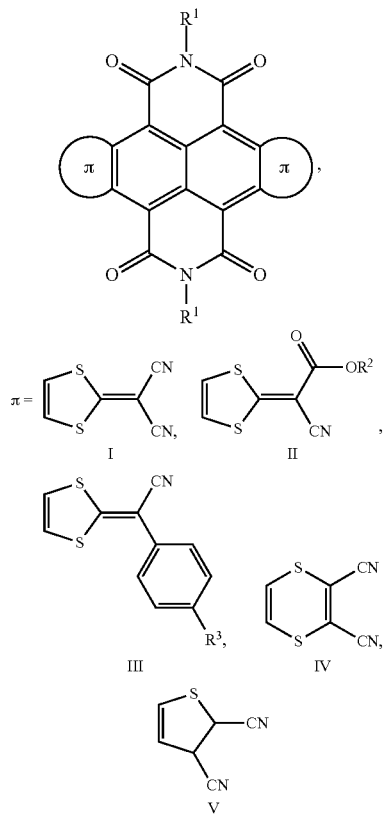

wherein, $R^1$ and $R^2$ are $C_1$~$C_{30}$ and $C_1$~$C_{12}$ n-alkyl or branched alkyl, respectively; $R^1$ is preferably $C_8$~$C_{24}$ n-alkyl or branched alkyl, more preferably $C_{12}$~$C_{24}$ n-alkyl or branched alkyl, still preferably $C_8$, $C_{12}$, $C_{14}$, $C_{16}$, $C_{17}$, $C_{20}$, and $C_{24}$ n-alkyl or branched alkyl, specific examples of $R^1$ are, such as, n-octyl, 2-ethylhexyl, 2-butyloctyl, 2-hexyloctyl, 2-hexyldecyl, 3-hexylundecyl, 2-octyldodecyl, 2-decyltetradecyl; $R^2$ is preferably $C_2$~$C_8$ alkyl, more preferably $C_2$~$C_6$ alkyl, examples of $R^2$ include, ethyl, n-hexyl, 2-ethylhexyl, and the like; $R^3$ is H or halogen, preferably H or bromo.

Class I compounds are 2-(1,3-dithiacyclopenten-2-ylidene)-2-malononitrile fused naphthalenetetracarboxylic derivatives; class II compounds are alkyl 2-(1,3-dithiacyclopenten-2-ylidene)-2-cyanoacetate fused naphthalenetetracarboxylic acid diimide derivatives; class III compounds are 2-(1,3-dithiacyclopenten-2-ylidene)-2-phenyl acetonitrile fused naphthalenetetracarboxylic acid diimide derivatives; class IV compounds are 1,4-dithiacyclohexen-2,3-dicarbonitrile fused naphthalenetetracarboxylic acid diimide derivatives; class V compounds are α,β-dicyanothiophene fused naphthalenetetracarboxylic acid diimide derivatives (non separable cis-trans isomers)

The following description further describes the aforementioned sulfur containing heterocycle fused naphthalenetetracarboxylic acid diimide derivatives:

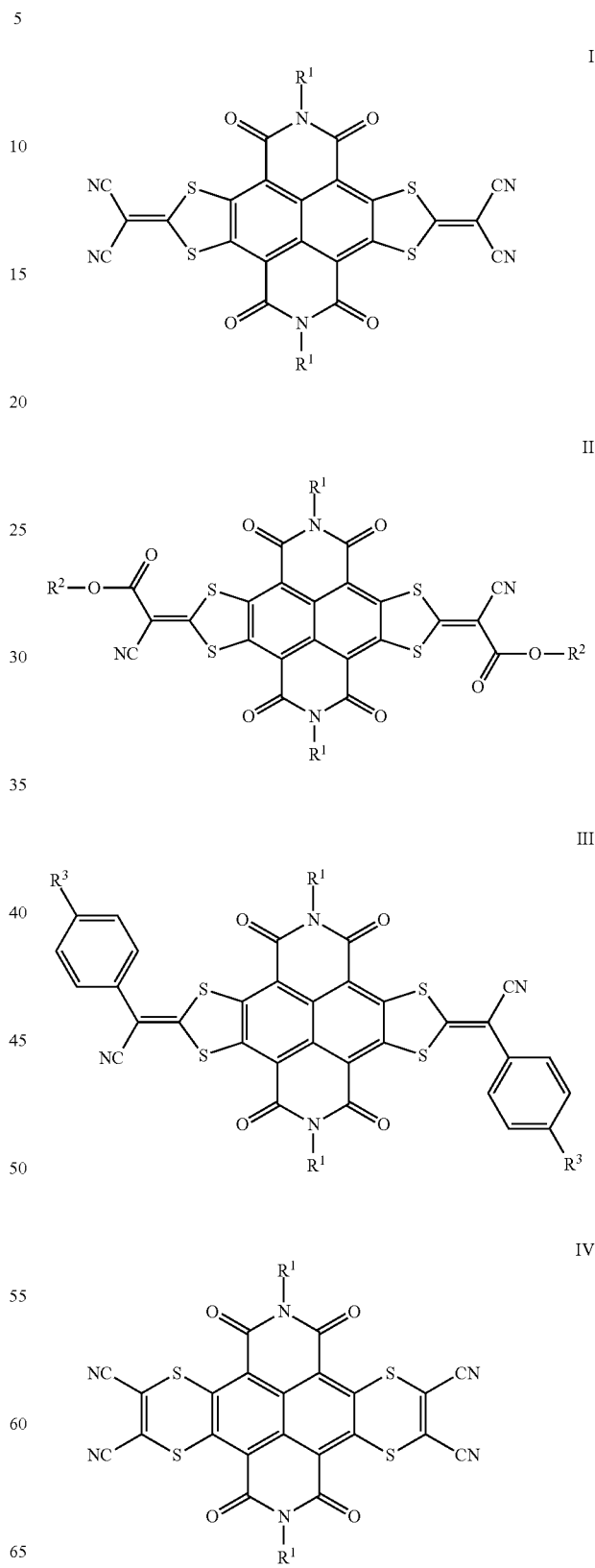

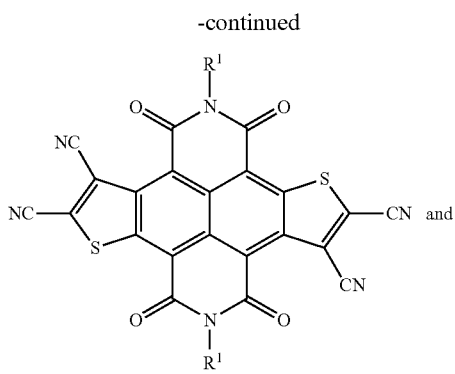

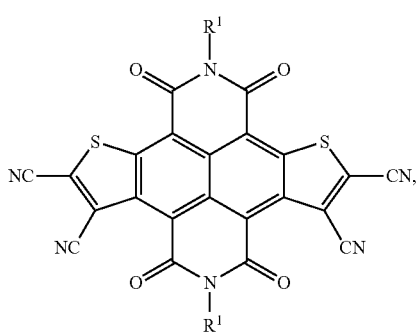

wherein R¹, R², and R³ are as defined above.

The present invention provides the methods for producing 5 classes of sulfur containing heterocycle fused naphthalenetetracarboxylic acid diimide derivatives. The recommended procedures are as below:

(A) Reacting 2,2-dicyano-ethylene-1,1-dithiol sodium with N-alkyl (R¹) substituted 2,3,6,7-tetrabromonaphthalenetetracarboxylic acid diimide of general formula (VI) at a molar ratio of 2.5~4:1 in an organic solvent, such as benzene, toluene, xylene, acetic acid, tetrahydrofuran, dioxane or N,N-dimethylformamide, for 0.5~2 hours at room temperature followed by 0.5~1 hour at 40~60° C. or simply reacting at room temperature for 1~6 hours;

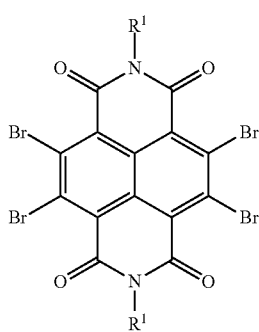

(B) Reacting alkyl cyanoacetate ($CNCH_2COOR_2$) or phenyl acetonitrile or 4-halo-phenyl acetonitrile with sodium hydride (NaH) and carbon disulfide ($CS_2$) at a molar ratio of 1:2~3:1~1.5 (molar ration of 1:2~2.1:1~1.1 is further recommended) in an organic solvent, such as tetrahydrofuran, dioxane or N,N-dimethylformamide, for 0.5~1 hour at 0~5° C. followed by 2~4 hours at room temperature, obtaining alkyl 2-cyanoacetate-ethylene-1,1-dithiol sodium or 2-phenyl acetonitrile-ethylene-1,1-dithiol sodium or 2-(4-halophenyl acetonitrile)-ethylene-1,1-dithiol sodium;

(C) Adding N-alkyl (R¹) substituted 2,3,6,7-tetrabromonaphthalenetetracarboxylic acid diimide of general formula VI into the reaction liquid produced in step (B) containing alkyl 2-cyanoacetate-ethylene-1,1-dithiol sodium or 2-phenyl acetonitrile-ethylene-1,1-dithiol sodium or 2-(4-halophenyl acetonitrile)-ethylene-1,1-dithiol sodium with a molar ratio of the diimide to $CS_2$ in step (B) at 1:5~10, and reacting for 0.5~2 hours at room temperature;

D) Reacting N-alkyl (R¹) substituted 2,3,6,7-tetrabromonaphthalenetetracarboxylic acid diimide with 1,2-dicyanoethylene-1,2-dithiol sodium (those purchased from TCI or synthesized according to *Inorg. Synth.* 1967, 10, 8. are recommended) at a molar ratio of 1:2~3.5 in an organic solvent, such as tetrahydrofuran, dioxane or N,N-dimethylformamide, for 0.5~1 hour at room temperature;

E) Adding the compound produced in step (D) and hydrogen peroxide (preferably 30% hydrogen peroxide) of 1:50~80 (molar ratio) into an acid, such as acetic acid or propanoic acid, and heating to 100~120° C. for 0.5~1.5 hours with stirring.

Recommendations:

In said method, the organic solvent is preferably benzene, toluene, xylene, acetic acid, tetrahydrofuran, dioxane or N,N-dimethylformamide.

In said method, the 2,2-dicyano-ethylene-1,1-dithiol sodium in step (A) is synthesized according to *J. Org. Chem.* 1964, 29, 660-665.

In said method, the reactions in steps (A)~(D) are conducted under the protection of an inert gas (high purity nitrogen or argon).

In said method, the alkyl cyanoacetate ($CNCH_2COOR^2$) in step (B) is synthesized according to *Adv. Synth. Catal.* 2005, 347, 33-38.

In said method, the N-alkyl (R¹) substituted 2,3,6,7-tetrabromonaphthalenetetracarboxylic acid diimide, i.e. the reactant in step (A), (C) and (D), is synthesized according to the method disclosed in *Org. Lett.* 2007, 9, 3917-3920.

In said method, the product from step (A) is 2-(1,3-dithiacyclopenten-2-ylidene)malononitrile fused naphthalenetetracarboxylic derivatives (Class I compounds, wherein R¹ is $C_1$~$C_{30}$ n-alkyl or branched alkyl).

In said method, the product from step (C) is alkyl 2-(1,3-dithiacyclopenten-2-ylidene)-2-cyanoacetate fused naphthalenetetracarboxylic acid diimide (Class II compounds, wherein R¹ and R² are $C_1$~$C_{30}$ and $C_1$~$C_{12}$ n-alkyl or branched alkyl, respectively) or 2-(1,3-dithiacyclopenten-2-ylidene)-2-phenyl acetonitrile fused naphthalenetetracarboxylic acid diimide derivatives (Class III compounds, wherein R¹ is $C_1$~$C_{30}$ n-alkyl or branched alkyl, and R³ is H or halogen).

In said method, the product from step (D) is 1,4-dithiacyclohexadiene-2,3-dicarbonitrile fused naphthalenetetracarboxylic acid diimide derivatives (Class IV compounds, wherein R¹ is $C_1$~$C_{30}$ n-alkyl or branched alkyl).

In said method, the product from step (E) is α,β-dicyanothiophene fused naphthalenetetracarboxylic acid diimide derivatives (Class V compounds, non separable cis-trans isomers, wherein $R^1$ is $C_1$–$C_{30}$ n-alkyl or branched alkyl).

In said method, the target compounds obtained from steps (A), (C), (D) and (E) are purified by silica gel chromatography column, using dichloromethane/petroleum ether or toluene/petroleum ether mixture as an eluent, with a yield of 30~86%.

In said method, the novel compounds obtained from steps (A), (C), (D) and (E) are characterized by one or more of mass spectrometry (MS-TOF), hydrogen nuclear magnetic resonance spectrum ($^1$H-NMR), carbon nuclear magnetic resonance spectrum ($^{13}$C-NMR), and elemental analysis, and the structures are confirmed.

As shown in reaction formula (I) in Examples, the present invention provided compounds 1~21, which are some of the exemplary compounds for the 5 classes of sulfur containing heterocycle fused naphthalenetetracarboxylic acid diimide derivatives (class I~V), and the synthetic scheme for their production. Examples 1~8 are eight exemplary compounds of 2-(1,3-dithiacyclopenten-2-ylidene)malononitrile fused naphthalenetetracarboxylic derivatives (class I compound), wherein $R^1$ is 2-decyltetradecyl, 2-octyldodecyl, 2-hexyldecyl, 2-hexyloctyl, 2-butyloctyl, 2-ethylhexyl, 3-hexylundecyl and n-octyl, respectively. Examples 9~11 are three exemplary compounds of alkyl 2-(1,3-dithiacyclopenten-2-ylidene)-2-cyanoacetate fused naphthalenetetracarboxylic acid diimide derivatives (class II compounds), wherein the substituents $R^1$ and $R^2$ are 2-octyldodecyl and ethyl; 2-octyldodecyl and n-hexyl; n-octyl and 2-ethylhexyl, respectively. Examples 12 (wherein $R^1$ and $R^2$ are 2-decyltetradecyl and H) and 13 (wherein $R^1$ and $R^2$ are 2-octyldodecyl and Br) are two exemplary compounds of 2-(1,3-dithiacyclopenten-2-ylidene)-2-phenyl acetonitrile fused naphthalenetetracarboxylic acid diimide derivatives (class III compounds). Examples 14~17 are four exemplary compounds of 1,4-dithiacyclohexadiene-2,3-dicarbonitrile fused naphthalenetetracarboxylic acid diimide derivatives (class IV compounds), wherein substituent $R^1$ is 2-decyltetradecyl, 2-octyldodecyl, 2-butyloctyl and n-octyl, respectively. Examples 18~21 are four exemplary compounds of α,β-dicyanothiophene fused naphthalenetetracarboxylic acid diimide derivatives (class V compounds, non separable cis-trans isomers), wherein the substituent $R^1$ is 2-decyltetradecyl, 2-octyldodecyl, 2-butyloctyl and n-octyl, respectively.

The sulfur containing heterocycle fused naphthalenetetracarboxylic acid diimide derivatives according to the present invention can be used in the fabrication of organic electronic devices, for example, used as a semiconducting layer to fabricate organic thin-film transistors or used in the preparation of organic solar cells.

Compounds 1~21 are analyzed by ultraviolet spectrometry (UV) for their photophysical properties and by cyclic voltammetry (CV) for their electrochemical properties, and organic thin-film transistor devices are fabricated based compounds 1-5, 7, 9, 10, 15 and 18 by solution processing.

The following examples are provided to assist the better understanding of the present invention and are not to be construed as limiting the scope of the disclosed invention.

(1) Methods for the preparation of exemplary compounds 1-21 (class I: 1-8; class II: 9~11; class III: 12 and 13; class IV: 14~17; class V: 18~21)

The synthetic scheme for Examples 1-21 is as shown in the reaction formula below:

Reaction Formula (1) for precursors

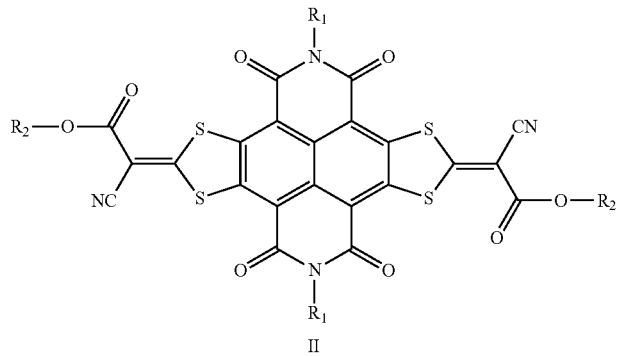

9: $R_1$ = 2-octyldodecyl, $R_2$ = ethyl
10: $R_1$ = 2-octyldodecyl, $R_2$ = n-hexyl
11: $R_1$ = n-octyl, $R_2$ = 2-ethylhexyl

-continued

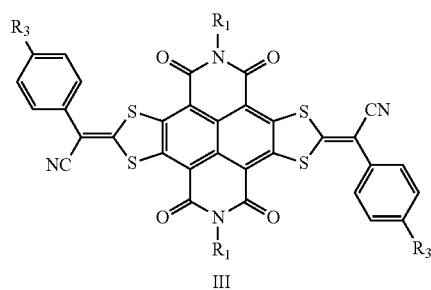

III

12: $R_1$ = 2-decyltetradecyl, $R_3$ = H
13: $R_1$ = 2-octyldodecyl, $R_3$ = Br

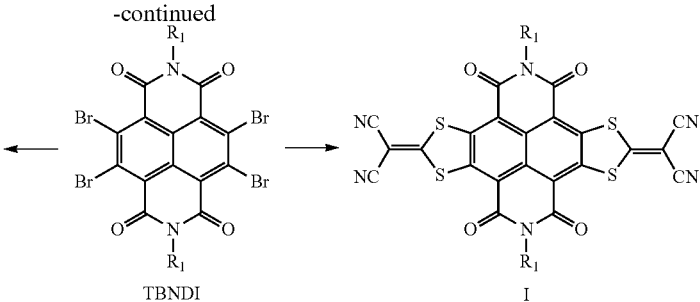

TBNDI
22: $R_1$ = 2-decyltetradecyl
23: $R_1$ = 2-octyldodecyl
24: $R_1$ = 2-hexyldecyl
25: $R_1$ = 2-hexyloctyl
26: $R_1$ = 2-butyloctyl
27: $R_1$ = 2-ethylhexyl
28: $R_1$ = 3-hexylundecyl
29: $R_1$ = n-octyl I
1: $R_1$ = 2-decyltetradecyl
2: $R_1$ = 2-octyldodecyl
3: $R_1$ = 2-hexyldecyl
4: $R_1$ = 2-hexyloctyl
5: $R_1$ = 2-butyloctyl
6: $R_1$ = 2-ethylhexyl
7: $R_1$ = 3-hexylundecyl
8: $R_1$ = n-octyl

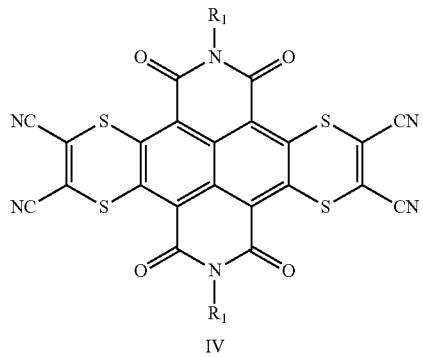

IV
14: $R_1$ = 2-decyltetradecyl
15: $R_1$ = 2-octyldodecyl
16: $R_1$ = 2-butyloctyl
17: $R_1$ = n-octyl

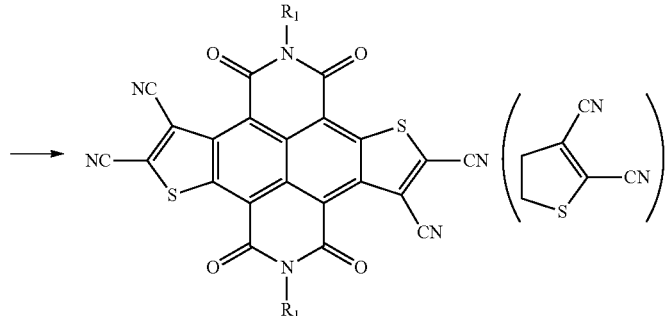

V
18: $R_1$ = 2-decyltetradecyl
19: $R_1$ = 2-octyldodecyl
20: $R_1$ = 2-butyloctyl
21: $R_1$ = n-octyl Synthesis of starting material: 2,3,6,7-tetrabromonaphthalenetetracarboxylic acid diimide derivatives (TBNDI: 22~29, whose chemical structures are illustrated below)

-continued

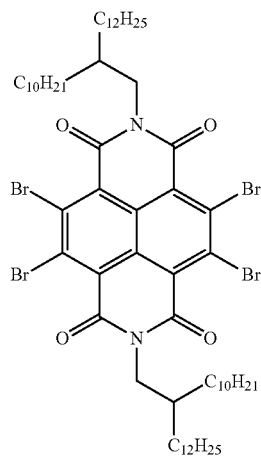

22

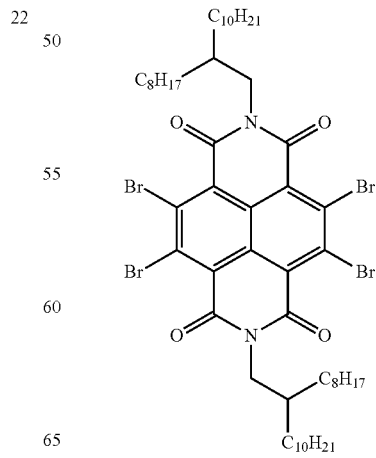

23

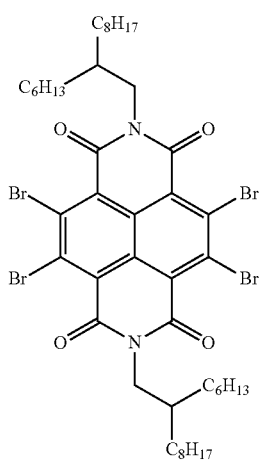

24

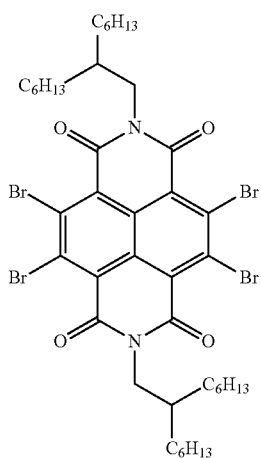

25

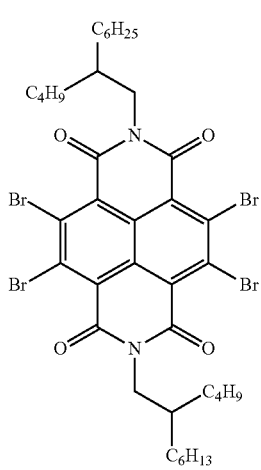

26

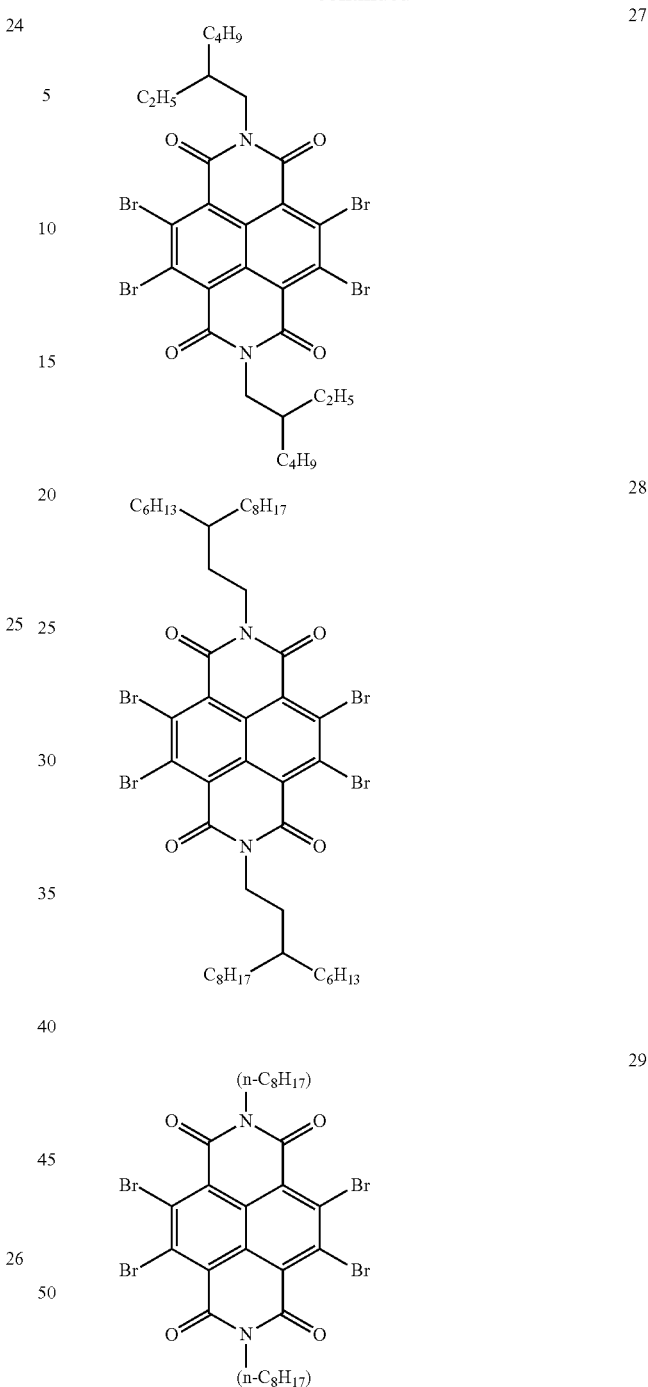

2,3,6,7-tetrabromonaphthalenetracarboxylic acid dianhydride (TBNDA) and N,N'-di(n-octyl)-2,3,6,7-tetrabromonaphthalene-1,4,5,8-tetracarboxylic acid diimide (29) were synthesized according to *Org. Lett.* 2007, 9, 3917~3920; 2-decyltetradecyl amine, 2-octyldodecyl amine, 2-hexyldecyl amine, 2-butyloctyl amine were synthesized according to the process reported in *Org. Lett.* 2008, 10, 5333~5336; 2-hexyloctyl amine was synthesized according to the process disclosed in U.S. Pat. No. 2,361,524; 3-hexylundecyl amine was synthesized according to the process reported in *J. Org. Chem.* 1961, 26, 3980~3987; 2-ethylhexyl amine is purchased from Aldrich.

Synthesis of N,N'-di(2-decyltetradecyl)-2,3,6,7-tetrabromonaphthalene-1,4,5,8-tetracarboxylic acid diimide (22)

TBNDA (3.3 g, 5.7 mmol) and 2-decyl-tetradecyl amine (6.5 g, 18.4 mmol) were added into acetic acid (50 mL) under nitrogen atmosphere, heated to 120° C. Heating was terminated when the reaction liquid turned clear and before the color got dark (the heating lasted for about 0.5~1 hour). After cooled to room temperature, the reaction solution was poured into water (400 mL) and filtered. The resulting precipitate was washed with water (200 mL), and dried under vacuum to obtain a yellow solid. The yellow solid and phosphorus tribromide (2.0 mL, 21.1 mmol) were added into anhydrous toluene (120 mL) and heated to reflux for 1 hour. After cooled to room temperature, the reaction liquid was poured into water (400 mL) and extracted with toluene (200 mL×3). The organic phases were combined and the solvent was evaporated under reduced pressure. The crude product was purified by silica gel chromatography column using dichloromethane/petroleum ether (1/2) as an eluent to give 1.35 g of a yellow solid (22), and the yield was 19% (calculated based on TBNDA as a starting material).

MS (MALDI-TOF) m/z 1257.6 (M$^+$);

$^1$H-NMR (300 MHz, CDCl$_3$) δ (ppm): 0.852-0.894 (m, 6H, —CH$_3$), 1.287-1.409 (m, 8H, CH$_2$), 1.235 (b, 40H, CH$_2$), 1.970-2.005 (m, 1H, CH), 4.159-4.184 (d, J=7.50 Hz, 2H, —CH$_2$—N);

$^{13}$C-NMR (100 MHz, CDCl$_3$): δ 14.10, 22.67, 26.25, 29.33, 29.56, 29.64, 30.01, 31.50, 31.90, 36.50, 46.60, 125.75, 126.32, 135.23, 160.18 (CO).

Synthesis of N,N'-di(2-octyldodecyl)-2,3,6,7-tetrabromonaphthalene-1,4,5,8-tetracarboxylic acid diimide (23)

The same synthetic method for compound 22 was used except using 2-octyldodecyl amine instead of 2-decyltetradecyl amine, and the yield was 33% (calculated based on the TBNDA as a starting material).

MS (MALDI-TOF) m/z 1144.8 (M$^+$);

$^1$H-NMR (300 MHz, CDCl$_3$) δ (ppm): 0.863-0.888 (m, 6H, —CH$_3$), 1.235 (b, 32H, CH$_2$), 1.966-2.008 (m, 1H, CH), 4.159-4.183 (d, J=7.20 Hz, 2H, —CH$_2$—N);

$^{13}$C-NMR (100 MHz, CDCl$_3$): δ 13.96, 22.52, 26.12, 29.15, 29.18, 29.38, 29.42, 29.87, 31.38, 31.73, 36.36, 46.46, 125.62, 126.18, 135.10, 160.05 (CO).

Synthesis of N,N'-di(2-hexyldecyl)-2,3,6,7-tetrabromonaphthalene-1,4,5,8-tetracarboxylic acid diimide (24)

The same synthetic method for compound 22 was used except using 2-hexyldecyl amine instead of 2-decyltetradecyl amine, and the yield was 18% (calculated based on TBNDA as a starting material).

MS (MALDI-TOF) m/z: 1030.9 (M$^+$);

$^1$H-NMR (300 MHz, CDCl$_3$) δ (ppm): 0.835-0.878 (m, 6H, —CH$_3$), 1.238-1.305 (m, 24H, —CH$_2$—), 1.975 (m, 1H, CH), 4.147-4.172 (d, 2H, J=7.50 Hz, —CH$_2$—N);

$^{13}$C-NMR (100 Hz, CDCl$_3$): δ 14.108, 14.122, 22.668, 26.275, 26.298, 29.316, 29.539, 29.715, 30.029, 31.562, 31.599, 31.807, 31.895, 36.557, 46.645, 125.816, 126.381, 135.284, 160.247 (C=O).

Synthesis of N,N'-di(2-hexyloctyl)-2,3,6,7-tetrabromonaphthalene-1,4,5,8-tetracarboxylic acid diimide (25)

The same synthetic method for compound 22 was used except using 2-hexyloctyl amine instead of 2-decyltetradecyl amine, and the yield was 22% (calculated based on TBNDA as a starting material).

MS (MALDI-TOF) m/z: 976.2 (M+H)$^+$;

$^1$H-NMR (300 MHz, CDCl$_3$) δ (ppm): 0.834-0.876 (m, 6H, —CH$_3$), 1.252-1.363 (m, 20H, —CH$_2$—), 1.963-1.991 (m, 1H, CH), 4.157-4.181 (d, 2H, J=7.20 Hz, —CH$_2$—N);

$^{13}$C-NMR (100 Hz, CDCl$_3$): δ 14.076, 22.636, 26.252, 29.687, 31.562, 31.779, 36.557, 46.617, 125.821, 126.386, 135.288, 160.260 (C=O).

Synthesis of N,N'-di(2-butyloctyl)-2,3,6,7-tetrabromonaphthalene-1,4,5,8-tetracarboxylic acid diimide (26)

The same synthetic method for compound 22 was used except using 2-butyloctyl amine instead of 2-decyltetradecyl amine, and the yield was 25% (calculated based on TBNDA as a starting material).

MS (MALDI-TOF) m/z: 918.9 (M$^+$), 940.9 (M+Na)$^+$;

$^1$H-NMR (300 MHz, CDCl$_3$) δ (ppm): 0.834-0.902 (m, 6H, —CH$_3$), 1.251-1.365 (m, 16H, —CH$_2$—), 1.955-2.002 (m, 1H, CH), 4.163-4.186 (d, 2H, J=6.90 Hz, —CH$_2$—N).

$^{13}$C-NMR (100 Hz, CDCl$_3$): δ 13.085, 13.110, 21.668, 22.101, 25.278, 27.502, 28.724, 30.267, 30.585, 30.812, 35.557, 45.638, 124.832, 125.397, 134.285, 159.270 (C=O).

Synthesis of N,N'-di(2-ethylhexyl)-2,3,6,7-tetrabromonaphthalene-tetracarboxylic acid diimide (27)

The same synthetic method for compound 22 was used except using 2-ethylhexyl amine instead of 2-decyltetradecyl amine, and the yield was 33% (calculated based on TBNDA as a starting material).

MS [MALDI (TOF)] m/z: 806.8 (M$^+$), 884.3 (M+2K—H)$^+$.

$^1$H-NMR (300 MHz, CDCl$_3$) δ (ppm): 0.859-0.969 (m, 6H), 1.287-1.409 (m, 8H), 1.923-1.967 (m, 1H), 4.169-4.194 (d, J=7.50 Hz, 2H).

Synthesis of N,N'-di(3-hexylundecyl)-2,3,6,7-tetrabromonaphthalene-1,4,5,8-tetracarboxylic acid diimide (28)

The same synthetic method for compound 22 was used except using 3-hexylundecyl amine instead of 2-decyltetradecyl amine, and the yield was 31% (calculated based on TBNDA as a starting material).

MS (MALDI-TOF) m/z: 1060.2 (M+H)$^+$;

$^1$H-NMR (300 MHz, CDCl$_3$) δ (ppm): 0.889-0.901 (m, 6H, —CH$_3$), 1.280-1.326 (m, 24H, —CH$_2$—), 1.463 (br, 1H, CH), 1.648-1.722 (m, 2H), 4.187-4.239 (m, 2H, —CH$_2$—N).

$^{13}$C-NMR (100 MHz, CDCl$_3$): δ 14.416, 22.976, 26.869, 26.899, 29.638, 29.928, 29.995, 30.330, 32.080, 32.184, 32.206, 33.784, 36.315, 41.555, 125.878, 126.815, 135.681, 159.895 (C=O).
Class I Compounds
Examples 1-8 (Chemical Structures are Illustrated Below)
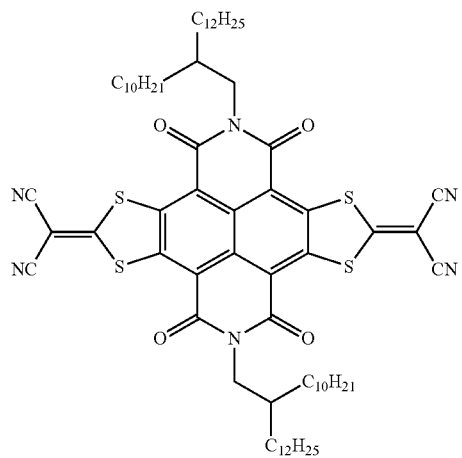
1
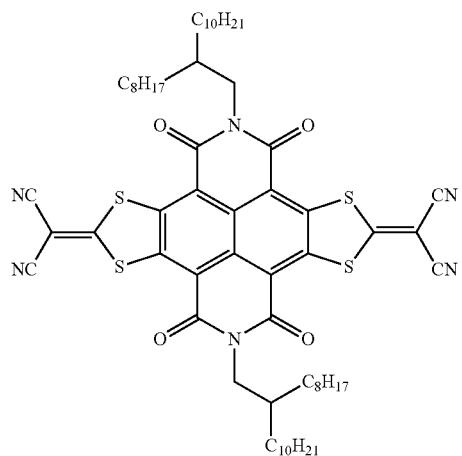
2
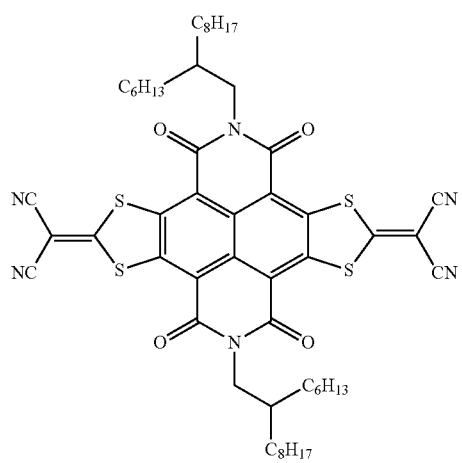
3
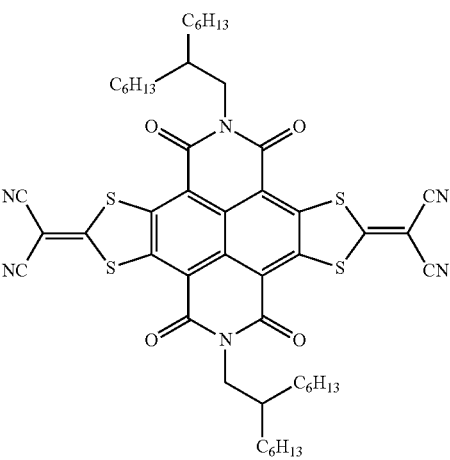
4
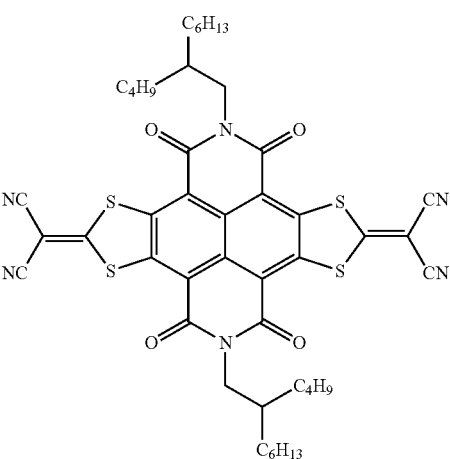
5
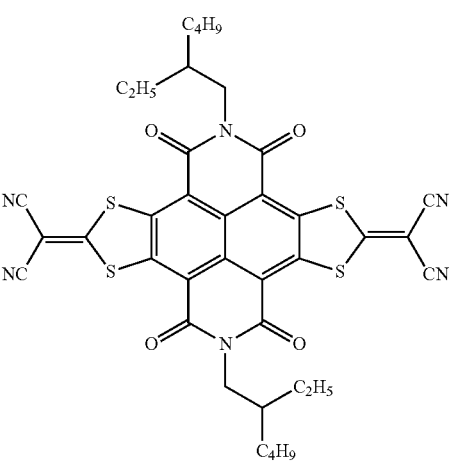
6

-continued

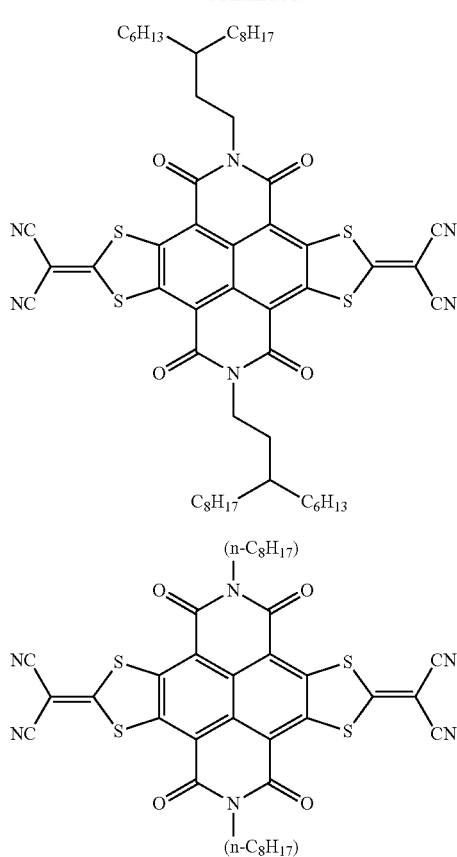

Example 1

Synthesis of N,N'-di(2-decyltetradecyl)-[2,3-d:6,7-d']-bi[2-(1,3-dithiacyclopenten-2-ylidene)-2-malononitrile]-naphthalene-1,4,5,8-tetracarboxylic acid diimide (1)

N,N'-di(2-decyltetradecyl)-2,3,6,7-tetrabromonaphthalene-1,4,5,8-tetracarboxylic acid diimide (22) (126 mg, 0.1 mmol), 2,2-dicyanoethylene-1,1-dithiol disodium (56 mg, 0.3 mmol), and tetrahydrofuran (20 mL) were added into a 100 ml three-neck flask, reacted at 50° C. for 1 hour, then the solvent was removed by a rotary evaporator under reduced pressure. The crude product was purified by silica gel chromatography column using dichloromethane/petroleum ether (3/1) as an eluent to give 60 mg of a purple black solid (compound 1), and the yield was 50%. Mp: 240° C. (from DSC);

MS (MALDI-TOF) m/z 1215.8 (M$^+$);

$^1$H-NMR (300 MHz, CDCl$_3$) δ (ppm): 0.849-0.889 (m, 6H, —CH$_3$), 1.231 (b, 40H, CH$_2$), 1.988-2.014 (m, 1H, CH), 4.219-4.244 (d, J=7.50 Hz, 2H, —CH$_2$—N);

$^{13}$C-NMR (100 MHz, CDCl$_3$): δ 14.11, 22.68, 26.28, 29.34, 29.57, 29.64, 30.01, 31.49, 31.91, 36.59, 46.49, 71.22 (=C(CN)$_2$), 111.58, 111.72 (CN), 125.09, 145.33, 161.96 (C=O), 181.93 (=CS$_2$);

Elemental analysis: calcd. for C$_{70}$H$_{98}$N$_6$O$_4$S$_4$: C, 69.15; H, 8.12; N, 6.91. found: C, 69.41; H, 8.37; N, 6.67.

Example 2

Synthesis of N,N'-di(2-octyldodecyl)-[2,3-d:6,7-d']-bi[2-(1,3-dithiacyclopenten-2-ylidene)-2-malononitrile]-naphthalene-1,4,5,8-tetracarboxylic acid diimide (2)

The same synthetic method for compound 1 was used except using 23 instead of 22, and the yield was 53%. Mp: 265° C. (from DSC);

MS (MALDI-TOF) m/z 1105.4 (M$^+$);

$^1$H-NMR (300 MHz, CDCl$_3$) δ (ppm): 0.840-0.891 (m, 6H, —CH$_3$), 1.236 (b, 32H, CH$_2$), 2.002-2.022 (m, 1H, CH), 4.222-4.246 (d, J=7.20 Hz, 2H, —CH$_2$—N);

$^{13}$C-NMR (100 MHz, CDCl$_3$): δ 14.13, 22.67, 22.69, 26.28, 29.30, 29.35, 29.52, 29.57, 29.65, 30.02, 31.49, 31.87, 31.93, 36.59, 46.48, 71.22 (=C(CN)$_2$), 111.60, 111.74 (CN), 125.10, 145.35, 161.97 (C=O), 181.95 (=CS$_2$);

Elemental analysis: calcd. for: C$_{62}$H$_{82}$N$_6$O$_4$S$_4$: C, 67.48; H, 7.49; N, 7.62. found: C, 67.38; H, 7.58; N, 7.56.

Example 3

Synthesis of N,N'-di(2-hexyldecyl)-[2,3-d:6,7-d']-bi[2-(1,3-dithiacyclopenten-2-ylidene)-2-malononitrile]-naphthalene-1,4,5,8-tetracarboxylic acid diimide (3)

The same synthetic method for compound 1 was used except using 24 instead of 22, and the yield was 54%. Mp: 317-319° C.;

MS (MALDI-TOF) m/z: 1036.4 (M+2Na—H)$^+$;

$^1$H-NMR (300 MHz, CDCl$_3$) δ (ppm): 0.845-0.869 (m, 6H, —CH$_3$), 1.249 (m, 24H, —CH$_2$—), 2.006 (m, 1H, CH), 4.220-4.245 (d, 2H, J=7.50 Hz, —CH$_2$—N);

$^{13}$C-NMR (100 Hz, CDCl$_3$): δ 14.039, 22.567, 22.613, 26.141, 26.233, 29.242, 29.460, 29.613, 29.951, 31.458, 31.710, 31.821, 36.566, 46.390, 71.224 (=C(CN)$_2$), 111.552 (C=N), 117.696, 125.071, 145.321, 161.932 (C=O), 181.862 (=CS$_2$).

Elemental analysis: calcd. for C$_{54}$H$_{66}$N$_6$O$_4$S$_4$: C, 65.42; H, 6.71; N, 8.48. found: C, 65.19; H, 6.60; N, 8.45.

Example 4

Synthesis of N,N'-di(2-hexyloctyl)-[2,3-d:6,7-d']-bi[2-(1,3-dithiacyclopenten-2-ylidene)-2-malononitrile]-naphthalene-1,4,5,8-tetracarboxylic acid diimide (4)

The same synthetic method for compound 1 was used except using 25 instead of 22, and the yield was 47%. Mp: 349-351° C.;

MS (MALDI-TOF) m/z: 937.0 (M+H)$^+$, 1089.0 (M+4K-3H)$^+$;

$^1$H-NMR (300 MHz, CDCl$_3$) δ (ppm): 0.849-0.892 (m, 6H, —CH$_3$), 1.268 (m, 20H, —CH$_2$—), 1.980-2.033 (m, 1H, CH), 4.221-4.246 (d, 2H, J=7.50 Hz, —CH$_2$—N);

$^{13}$C-NMR (100 Hz, CDCl$_3$): δ 14.097, 22.625, 26.201, 29.670, 31.503, 31.766, 36.639, 46.398, 71.336 (=C(CN)$_2$), 111.614 (C≡N), 117.724, 125.115, 145.383, 161.973 (C=O), 181.877 (=CS$_2$).

Elemental analysis: calcd. for: C$_{50}$H$_{58}$N$_6$O$_4$S$_4$: C, 64.21; H, 6.25; N, 8.99. found: C, 64.12; H, 6.20; N, 8.84.

Example 5

Synthesis of N,N'-di(2-butyloctyl)-[2,3-d:6,7-d']-bi[2-(1,3-dithiacyclopenten-2-ylidene)-2-malononitrile]-naphthalene-1,4,5,8-tetracarboxylic acid diimide (5)

The same synthetic method for compound 1 was used except using 26 instead of 22, and the yield was 68%. Mp: 369-371° C.;

MS (MALDI-TOF) m/z: 881.2 (M+H)$^+$, 1033.3 (M+4K-3H)$^+$;

H-NMR (300 MHz, CDCl$_3$) δ (ppm): 0.845-0.917 (m, 6H, —CH$_3$), 1.264 (m, 16H, —CH$_2$—), 2.011 (m, 1H, CH), 4.223-4.246 (d, 2H, J=6.90 Hz, —CH$_2$—N);

Elemental analysis: calcd. for: C$_{46}$H$_{50}$N$_6$O$_4$S$_4$: C, 62.84; H, 5.73; N, 9.56. found: C, 62.38; H, 5.55; N, 9.43.

Example 6

Synthesis of N,N'-di(2-ethylhexyl)-[2,3-d:6,7-d']-bi[2-(1,3-dithiacyclopenten-2-ylidene)-2-malononitrile]-naphthalene-1,4,5,8-tetracarboxylic acid diimide (6)

The same synthetic method for compound 1 was used except using 27 instead of 22, and the yield was 51%.

[MS (TOF)] m/z: 767.5 (M$^+$).

$^1$H-NMR (500 MHz, CDCl$_3$) δ (ppm): 0.89-0.92 (t, J=7.50 Hz, 3H), 0.94-0.97 (t, J=7.50 Hz, 3H), 1.29-1.42 (m, 8H), 1.96-1.98 (m, 1H), 4.20-4.28 (m, 2H).

Elemental analysis: calcd. for: C$_{38}$H$_{34}$N$_6$O$_4$S$_4$: C, 59.51; H, 4.47; N, 10.96. found: C, 59.51; H, 4.38; N, 10.84.

Example 7

Synthesis of N,N'-di(3-hexylundecyl)-[2,3-d:6,7-d']-bi[2-(1,3-dithiacyclopenten-2-ylidene)-2-malononitrile]-naphthalene-1,4,5,8-tetracarboxylic acid diimide (7)

The same synthetic method for compound 1 was used except using 28 instead of 22, and the yield was 65%. Mp: 330-332° C.;

MS (MALDI-TOF) m/z: 1018.7 M$^+$;

$^1$H-NMR (300 MHz, CDCl$_3$) δ (ppm): 0.860-0.903 (m, 6H, —CH$_3$), 1.254-1.311 (m, 24H, —CH$_2$—), 1.492 (br, 1H, CH), 1.702 (br, 2H), 4.262-4.324 (m, 2H, —CH$_2$—N);

$^{13}$C-NMR (100 MHz, CDCl$_3$): δ 14.408, 22.954, 22.976, 26.809, 26.891, 29.631, 29.899, 29.936, 30.286, 32.013, 32.139, 32.176, 33.702, 33.740, 36.308, 41.139, 71.397 (=C(CN)$_2$), 111.839 (C≡N), 118.151, 125.319, 145.425, 161.816 (C=O), 182.234 (=CS$_2$);

Elemental analysis: calcd. for: C$_{56}$H$_{70}$N$_6$O$_4$S$_4$: C, 65.98; H, 6.92; N, 8.24. found: C, 65.96; H, 7.10; N, 8.09.

Example 8

Synthesis of N,N'-di(n-octyl)-[2,3-d:6,7-d']-bi[2-(1,3-dithiacyclopenten-2-ylidene)-2-malononitrile]-naphthalene-1,4,5,8-tetracarboxylic acid diimide (8)

The same synthetic method for compound 1 was used except using 29 instead of 22, and the yield was 62%.

[MS (TOF)] m/z: 767.3 (M$^+$).

$^1$H-NMR (300 MHz, CDCl$_3$) δ (ppm): 0.864 (3H), 1.258-1.301 (m, 10H), 1.792 (m, 2H), 4.299 (t, 2H).

Elemental analysis: calcd. for C$_{38}$H$_{34}$N$_6$O$_4$S$_4$: C, 59.51; H, 4.47; N, 10.96. found: C, 59.45; H, 4.46; N, 10.58.

Class II Compounds

Examples 9-11 (Chemical Structures are Illustrated Below)

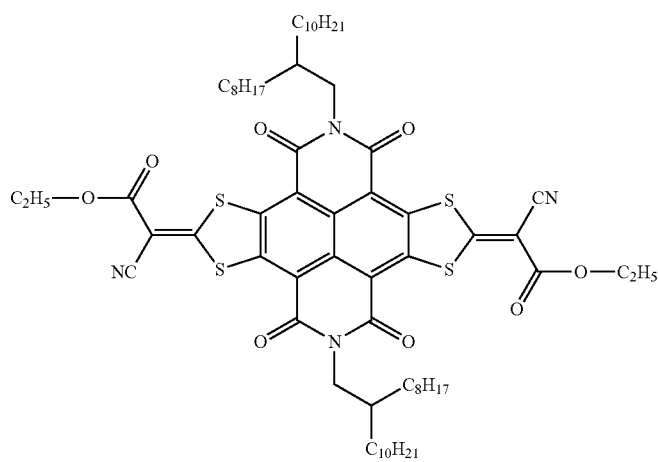

9

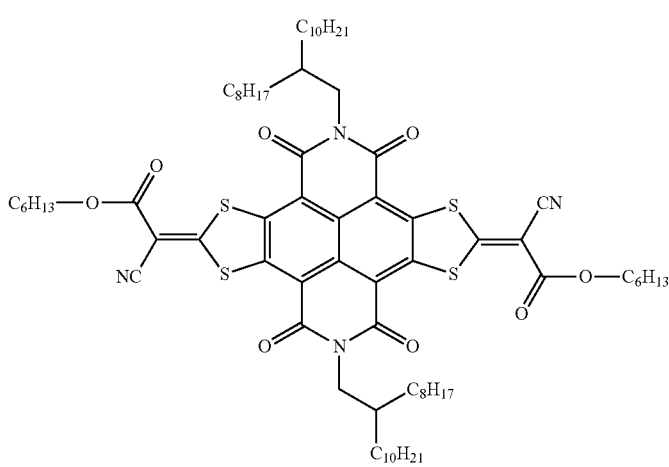

10

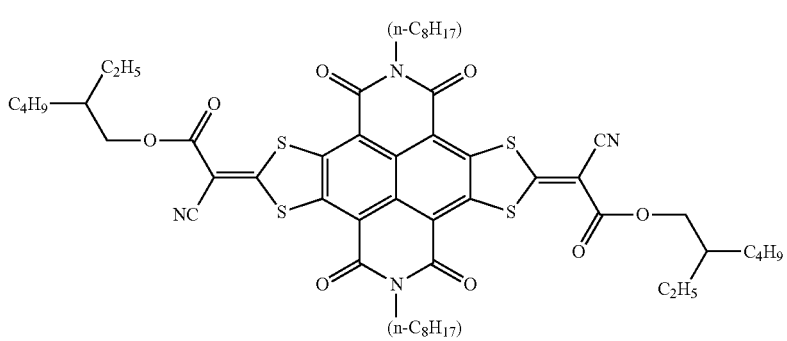

11

Example 9

Synthesis of N,N'-di(2-octyldodecyl)-[2,3-d:6,7-d']-bi[ethyl 2-(1,3-dithiacyclopenten-2-ylidene)-2-cyanoacetate]-naphthalene-1,4,5,8-tetracarboxylic acid diimide (9)

Detailed synthetic procedure was:

Ethyl cyanoacetate ($CNCH_3COOEt$, 297 mg, 2.63 mmol) and carbon disulfide ($CS_2$, 0.16 mL, 2.63 mmol) were dissolved in THF (25 mL), and under nitrogen atmosphere and at 0~5° C. the resulting solution was added slowly and dropwise into a three neck flask charged with sodium hydride (96% NaH, 132 mg, 5.3 mmol) and THF (5 mL) over 0.5 hour. The reaction liquid was warmed to room temperature, and kept stirring for 4 hours. 300 mg (0.26 mmol) of N,N'-di(2-octyldodecyl)-2,3,6,7-tetrabromonaphthalenetetracarboxylic acid diimide (23) was added to the reaction liquid and further reacted for another 0.5 hours, then the solvent was removed by a rotary evaporator under reduced pressure. The crude product was purified by silica gel chromatography column using dichloromethane/petroleum ether (V/V=3/2) as an eluent to give 270 mg of a dark red solid (compound 9), and the yield was 86%.

[MS (TOF)] m/z: 1196.6 ($M^+$).

$^1$H-NMR (300 MHz, $CDCl_3$) δ (ppm): 0.847-0.857 (m, 6H, $CH_3$), 1.224 (b, 32H, $CH_2$), 1.415-1.464 (t, J=7.35 Hz, 3H, ($OCH_2$)$CH_3$), 2.041 (b, 1H, CH), 4.228-4.252 (d, J=7.2 Hz, 2H, —$CH_2$—N), 4.398-4.467 (q, J=6.9 Hz, 2H, —$CH_2$—O).

$^{13}$C-NMR (100 Hz, $CDCl_3$): δ 14.076, 14.182, 22.650, 26.460, 29.344, 29.649, 30.094, 31.571, 31.909, 36.524, 46.339, 63.061 (—$CH_2OOC$), 91.232, 113.825 (C≡N), 116.954, 117.635, 117.866, 124.681, 143.181, 148.172, 161.824, 162.042, 162.417, 177.222 (=$CS_2$);

Elemental analysis: calcd. for $C_{66}H_{92}N_4O_8S_4$: C, 66.18; H, 7.74; N, 4.68. found: C, 66.24; H, 7.79; N, 4.45.

Example 10

Synthesis of N,N'-di(2-octyldodecyl)-[2,3-d:6,7-d']-bi[n-hexyl 2-(1,3-dithiacyclopenten-2-ylidene)-2-cyano acetate]-naphthalene-1,4,5,8-tetracarboxylic acid diimide (10)

Detailed synthetic procedure was:

The same synthetic method in Example 9 was used except using n-hexyl cyanoacetate instead of ethyl cyanoacetate to give a dark brown solid (10), and the yield was 59%.

[MS (TOF)] m/z: 1308.7 ($M^+$).

$^1$H-NMR (300 MHz, $CDCl_3$) δ (ppm): 0.854-0.942 (m, 9H, $CH_3$), 1.223-1.368 (m, 38H, $CH_2$), 1.741-1.832 (m, 2H, $CH_2$), 2.043 (b, 1H, CH), 4.227-4.251 (d, J=7.2 Hz, 2H, —$CH_2$—N), 4.335-4.378 (t, J=6.5 Hz, 2H, —$CH_2$—O).

$^{13}$C-NMR (100 Hz, $CDCl_3$): δ 13.997, 14.076, 22.501, 25.469, 26.455, 28.492, 29.344, 30.099, 31.261, 31.418, 31.566, 31.909, 36.515, 46.335, 67.154 (—$CH_2OOC$), 91.274, 113.825 (C≡N), 116.797, 117.005, 117.644, 117.862, 124.737, 143.278, 148.237, 161.852, 162.065, 162.491, 177.209 (=$CS_2$);

Elemental analysis: calcd. for $O_{74}H_{108}N_4O_8S_4$: C, 67.85; H, 8.31; N, 4.28. found: C, 67.87; H, 8.57; N, 3.85.

Example 11

Synthesis of N,N'-di(n-octyl)-[2,3-d:6,7-d']-bi[2-ethylhexyl 2-(1,3-dithiacyclopenten-2-ylidene)-2-cyanoacetate]-naphthalene-1,4,5,8-tetracarboxylic acid diimide (11)

Detailed synthetic procedure was:

The same synthetic method in Example 9 was used except using 2-ethylhexyl cyanoacetate and 29 instead of ethyl cyanoacetate and 23, respectively, to give a dark brown solid (11), and the yield was 41%.

[MS (TOF)] m/z: 1051.1 (M+Na)$^+$, 1074.1 (M+2Na—H)$^+$.

$^1$H-NMR (300 MHz, CDCl$_3$) δ (ppm): 0.926-0.932 (m, 9H, CH$_3$), 1.302 (b, 18H, CH$_2$), 1.784-1.814 (m, 3H, overlapped, CH$_3$CH$_2$CH and CH), 4.282-4.295 (m, 4H, overlapped, —CH$_2$—N and —CH$_2$—O).

Elemental analysis: calcd. for C$_{54}$H$_{68}$N$_4$O$_8$S$_4$: C, 63.01; H, 6.66; N, 5.44. found: C, 63.03; H, 6.61; N, 5.34.

Class III Compounds

Examples 12 and 13 (Chemical Structures are Illustrated Below)

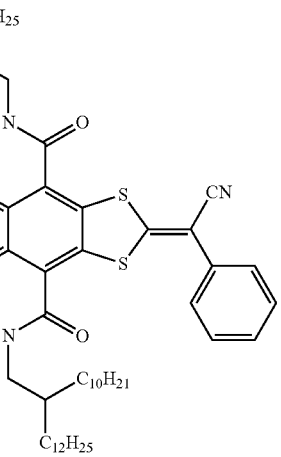

12

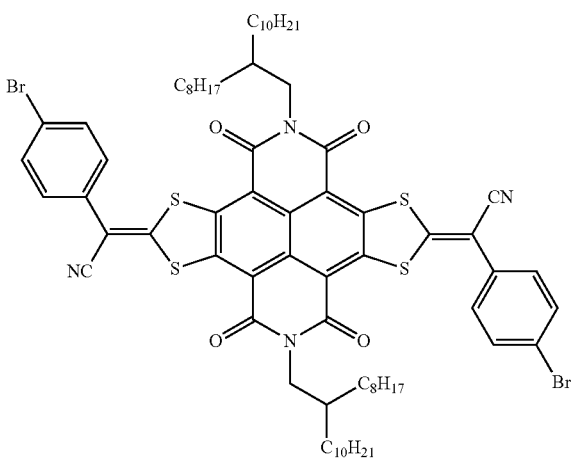

13

Example 12

Synthesis of N,N'-di(2-decyltetradecyl)-[2,3-d:6,7-d']-bi[2-(1,3-dithiacyclopenten-2-ylidene)-2-phenyl acetonitrile]-naphthalene-1,4,5,8-tetracarboxylic acid diimide (12)

Detailed synthetic procedure was:

Under nitrogen atmosphere, sodium hydride (96% NaH, 40.9 mg, 1.7 mmol), phenyl acetonitrile (92 μL, 0.8 mmol) and DMF (5 mL) were added into a 50 mL three-neck flask at 0~5° C., and reacted for 0.5 hour, followed by addition of carbon disulfide (53 μL, 0.88 mmol). The reaction liquid was warmed to room temperature, and further reacted for another 2 hours. N,N'-di(2-decyltetradecyl)-2,3,6,7-tetrabromonaphthalenetetracarboxylic acid diimide (20) (103 mg, 0.08 mmol) was added into the reaction liquid and reacted at room temperature for another 0.5 hours, then the reaction liquid was poured into water (100 mL), extracted with dichloromethane solution (50 mL×4). The organic phases were combine and dried, then the solvent was removed by a rotary evaporator under reduced pressure. The crude product was purified by silica gel chromatography column using dichloromethane/petroleum ether (V/V=4/5) as an eluent to give 52 mg of a blue purple solid (compound 12), and the yield was 48%.

[MS (TOF)] m/z: 1317.7 (M$^+$).

$^1$H-NMR (300 MHz, CDCl$_3$) δ (ppm): 0.837-0.878 (m, 6H, CH$_3$), 1.217 (b, 40H, CH$_2$), 2.014 (m, 1H, CH), 4.158-4.185 (m, 2H, —CH$_2$—N), 7.419-7.471 (m, 1H, Ar—H), 7.518-7.568, (m, 2H, Ar—H), 7.677-7.704, (d, J=8.1 Hz, 2H, Ar—H).

Example 13

Synthesis of N,N'-di(2-octyl-dodecyl)-[2,3-d:6,7-d']-bi[2-(1,3-dithiacyclopenten-2-ylidene)-2-(4-bromophenyl acetonitrile)]-naphthalene-1,4,5,8-tetracarboxylic acid diimide (13)

Detailed synthetic procedure was:

The same synthetic method in Example 12 was used except using 4-bromophenyl acetonitrile and 23 instead of phenyl acetonitrile and 22, respectively, to give a blue purple solid (13), and the yield was 60%.

[MS (TOF)] m/z: 1364.7 (M+H)$^+$.

¹H-NMR (300 MHz, CDCl₃) δ (ppm): 0.855 (b, 6H), 1.221 (b, 32H), 1.993 (b, 1H, CH), 4.165 (b, 2H, —CH₂—N), 7.580 (m, 2H, Ar—H), 7.664, (m, 2H, Ar—H).

Class IV Compounds

Examples 14-17 (Chemical Structures are Illustrated Below)

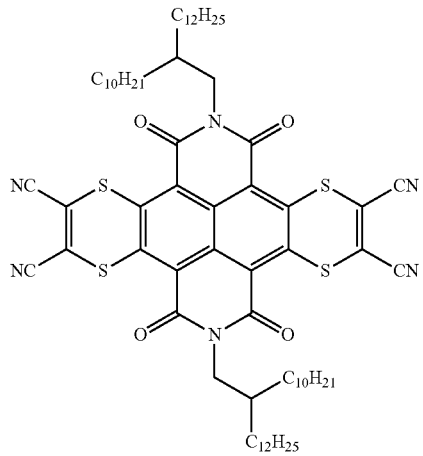

14

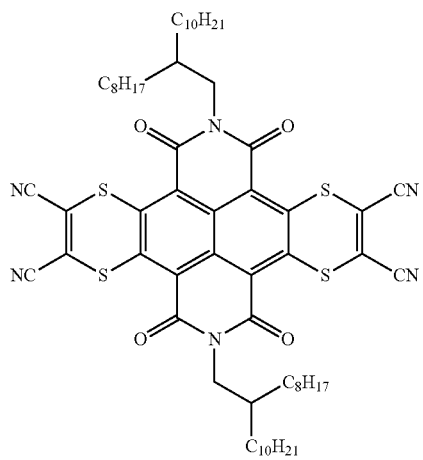

15

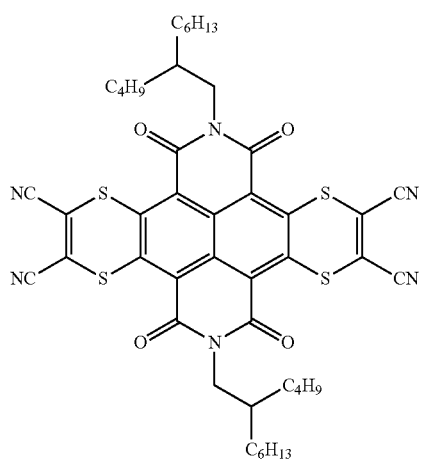

16

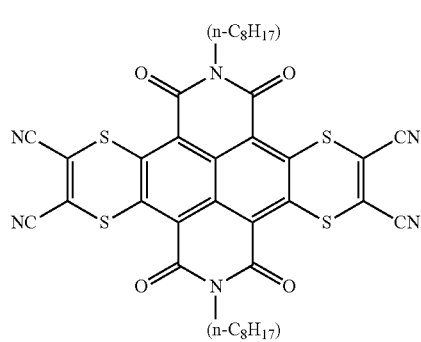

17

Example 14

Synthesis of N,N'-di(2-decyl-tetradecyl)-[2,3-d:6,7-d']-bi[1,4-dithiacyclohexadiene-2,3-dicarbonitrile]-naphthalene-1,4,5,8-tetracarboxylic acid diimide (14)

Under nitrogen atmosphere, 700 mg (0.56 mmol) of N,N'-di(2-decyl-tetradecyl)-2,3,6,7-tetrabromonaphthalenetetracarboxylic acid diimide (22), 313 mg (1.68 mmol) of 1,2-dicyanoethylene1,2-dithiol sodium (purchased from TCI) and 70 mL of tetrahydrofuran were added into a 100 ml three-neck flask, reacted for 1 hour and then the solvent was removed by a rotary evaporator under reduced pressure. The crude product was purified by silica gel chromatography column using toluene/petroleum ether (V/V=2/1) as an eluent to give 270 mg of a red solid (compound 14), and the yield was 39.6%.

[MS (TOF)] m/z: 1217.3 (M+H)⁺.

¹H-NMR (300 MHz, CDCl₃) δ (ppm): 0.852-0.895 (m, 6H, CH₃), 1.246 (b, 40H, CH₂), 1.929-1.970 (m, 1H, CH), 4.113-4.138 (d, J=7.5 Hz, 2H, —CH₂—N).

¹³C-NMR (100 Hz, CDCl₃): δ 13.109, 21.675, 25.097, 28.337, 28.578, 28.605, 28.643, 28.656, 28.685, 29.003, 30.444, 30.907, 35.569, 45.313, 110.373, 120.923, 122.111, 125.086, 139.321, 160.468; FT-IR (KBr, cm⁻¹) u 2922.7 (s), 2852.2, 2208.5 (C≡N).

Elemental analysis: calcd. for $C_{70}H_{98}N_6O_4S_4$: C, 69.15; H, 8.12; N, 6.91. found: C, 69.45; H, 7.96; N, 6.86.

Example 15

Synthesis of N,N'-di(2-octyl-dodecyl)-[2,3-d:6,7-d']-bi[1,4-dithiacyclohexadiene-2,3-dicarbonitrile]-naphthalene-1,4,5,8-tetracarboxylic acid diimide (15)

Detailed synthetic procedure was:
The same synthetic method in Example 14 was used except using 23 instead of 22 to give a red solid (15), and the yield was 34.5%.

[MS (TOF)] m/z: 1105.7 (M+H)⁺.

¹H-NMR (300 MHz, CDCl₃) δ (ppm): 0.871 (m, 6H, CH₃), 1.251 (b, 32H, CH₂), 1.951 (b, 1H, CH), 4.116-4.138 (d, J=6.6 Hz, 2H, —CH₂—N).

¹³C-NMR (100 Hz, CDCl₃): δ 14.085, 22.654, 26.108, 29.238, 29.316, 29.511, 29.557, 29.590, 29.622, 29.983, 31.474, 31.895, 36.576, 46.335, 111.367 (C≡N), 121.899 (=C(CN)S), 123.089, 126.103, 140.390, 161.478 (C=O);

Elemental analysis: calcd. for $C_{62}H_{82}N_6O_4S_4$: C, 67.48; H, 7.49; N, 7.62. found: C, 67.66; H, 7.35; N, 7.61.

Example 16

Synthesis of N,N'-di(2-butyloctyl)-[2,3-d:6,7-d']-bi[1,4-dithiacyclohexadiene-2,3-dicarbonitrile]-naphthalene-1,4,5,8-tetracarboxylic acid diimide (16)

Detailed synthetic procedure was:

The same synthetic method in Example 14 was used except using 26 instead of 22 to give a red solid (16), and the yield was 72.5%.

[MS (TOF)] m/z: 882.0 (M+H)$^+$, 902.0 (M+Na)$^+$.

$^1$H-NMR (500 MHz, CDCl$_3$) δ (ppm): 0.854-0.928 (m, 6H, CH$_3$), 1.281 (b, 16H, CH$_2$), 1.958 (b, 1H, CH), 4.121-4.145 (d, J=7.2 Hz, 2H, —CH$_2$—N).

Example 17

Synthesis of N,N'-di(n-octyl)-[2,3-d:6,7-d']-bi[1,4-dithiacyclohexadiene-2,3-dicarbonitrile]-naphthalene-1,4,5,8-tetracarboxylic acid diimide (17)

Detailed synthetic procedure was:

The same synthetic method in Example 14 was used except using 29 instead of 22 to give a red solid (17), and the yield was 66%.

[MS (TOF)] m/z: 769.9, (M+H)$^+$ $^1$H-NMR (500 MHz, CDCl$_3$) δ (ppm): 0.868-0.913 (t, J=6.75 Hz, 3H, CH$_3$), 1.253-1.400 (m, 10H, CH$_2$), 1.721-1.749 (m, 2H, CH$_2$), 4.149-4.199 (t, J=7.5 Hz, 2H, —CH$_2$—N).

Class V Compounds

Examples 18-21 (Chemical Structures are Illustrated Below, Non Separable Cis-Trans Isomers)

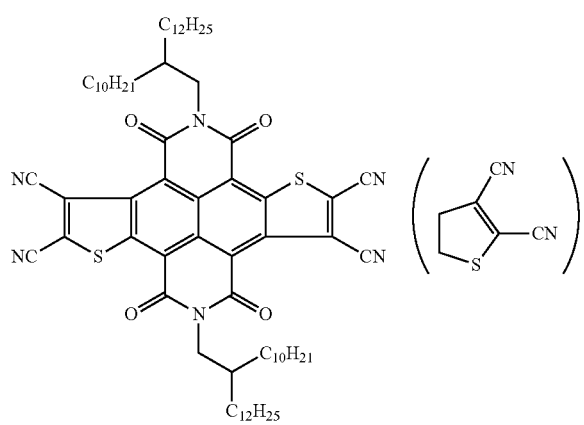

18

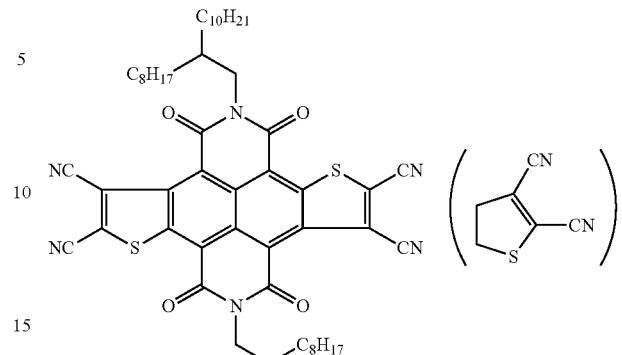

19

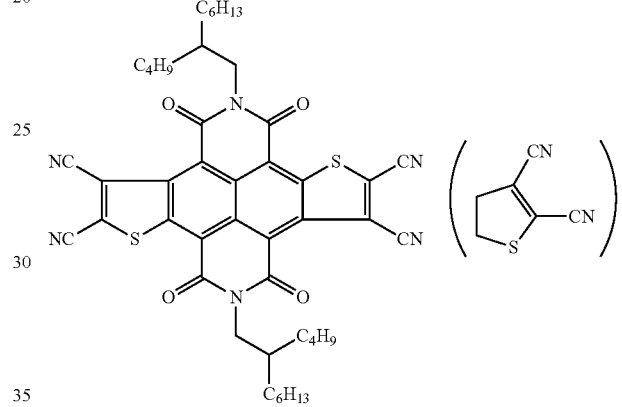

20

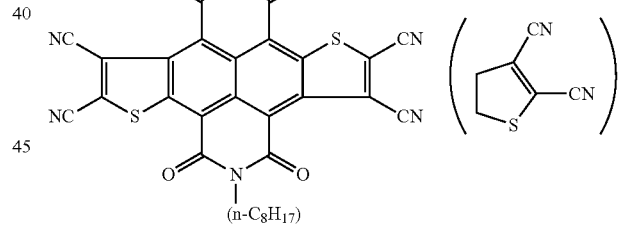

21

Example 18

Synthesis of N,N'-di(2-decyl-tetradecyl)-[2,3-d:6,7-d']-bi[α,β-dicyanothiophene]-naphthalene-1,4,5,8-tetracarboxylic acid diimide (18)

Detailed synthetic procedure was:

118 mg (0.1 mmol) of N,N'-di(2-decyl-tetradecyl)-[2,3-d:6,7-d']-bi[1,4-dithiacyclohexene-2,3-dicarbonitrile]-naphthalene-1,4,5,8-tetracarboxylic acid diimide (14) and 50 mL of propanoic acid were added into a 100 ml three-neck flask, heated while stirring to dissolve the solid, and then 1.74 mL of 30% H$_2$O$_2$ (17 mmol) was added into the reaction liquid and heated at 120° C. while stirring for 1 hour. After cooled to room temperature, the reaction liquid was poured into water (200 mL), and suction filtered. The resulting crude product was dried, and then purified by gel chromatography column using dichloromethane/petroleum ether (V/V=2/1) to give 34 mg of a bright red solid (compound 18), and the yield was 30%.

[MS (TOF)] m/z: 1174.6 (M+Na)$^+$, 1196.7 (M+2Na—H)$^+$, 1212.6 (M+Na+K—H)$^+$.

$^1$H-NMR (300 MHz, CDCl$_3$) δ (ppm): 0.848-0.890 (m, 6H, CH$_3$), 1.230-1.410 (m, br, 40H, CH$_2$), 2.055-2.134 (m, 1H, CH), 4.299-4.375 (m, 2H, CH$_2$—N).

$^{13}$C-NMR (100 Hz, CDCl$_3$): δ 14.134, 22.703, 26.215, 26.327, 26.485, 29.375, 29.605, 29.655, 29.679, 29.704, 30.002, 31.514, 31.590, 31.777, 31.932, 36.632, 46.126, 46.164, 46.617, 111.015, 111.059, 111.112, 111.314, 117.423, 117.794, 117.822, 119.807, 121.025, 123.652, 124.453, 135.969, 136.035, 136.872, 137.552, 143.576, 144.402, 161.244 (C=O), 162.558 (C=O);

Elemental analysis: calcd. for C$_{70}$H$_{98}$N$_6$O$_4$S$_2$: C, 73.00; H, 8.58; N, 7.30. found: C, 73.16; H, 8.55; N, 6.90.

Example 19

Synthesis of N,N'-di(2-octyl-dodecyl)-[2,3-d:6,7-d']-bi[α,β-dicyanothiophene]-naphthalene-1,4,5,8-tetra-carboxylic acid diimide (19)

The same synthetic method in Example 18 was used except using 15 instead of 14 to give a red solid (19), and the yield was 52%.

[MS (TOF)] m/z: 1142.0 (M+H)$^+$, 1064.0 (M+Na)$^+$, 1085.0 (M+2Na—H)$^+$, 1101.0 (M+Na+K—H)$^+$.

$^1$H-NMR (300 MHz, CDCl$_3$) δ (ppm): 0.837-0.867 (m, 6H, CH$_3$), 1.230-1.411 (m, 32H, CH$_2$), 2.053-2.127 (m, 1H, CH), 4.297-4.375 (m, 2H, CH$_2$—N).

Example 21

Synthesis of N,N'-di(n-octyl)-[2,3-d:6,7-d']-bi[α,β-dicyanothiophene]-naphthalene-1,4,5,8-tetracar-boxylic acid diimide (21)

The same synthetic method in Example 18 was used except using 17 instead of 14 to give a red solid (21), and the yield was 46.5%.

[MS (TOF)] m/z: 705.5 (M+H)$^+$, 727.5 (M+Na)$^+$, 748.5 (M+2Na—H)$^+$, 764.5 (M+Na+K—H)$^+$, 780.5 (M+2K—H)$^+$.

$^1$H-NMR (500 MHz, CDCl$_3$) δ (ppm): 0.864-0.896 (t, 3H, CH$_3$), 1.254-1.512 (m, 10H, CH$_2$), 1.799-1.903 (m, 2H, CH$_2$), 4.366-4.445 (m, 2H, CH$_2$—N).

The 21 exemplary compounds (1~21) described above for the five classes of sulfur containing heterocycle fused naphthalenetetracarboxylic acid diimide derivatives are soluble in regular organic solvents, such as chloroform, toluene, chlorobenzene, dichlorobenzene, and the like. At room temperature, the solubilities of all these compounds in common solvents, for example, chloroform, tetrahydrofuran, and others, are above 5 mg/mL, except for compounds 6 and 8, which have relatively low solubility.

(2) UV absorption spectrum and electrochemical properties of the exemplary compounds (1-21) for class I-V sulfur containing heterocycle fused naphthalenetetracarboxylic acid diimide derivatives UV absorption spectrum measurement was conducted using U-3900 spectrometer. Samples were dissolved in dichloromethane to a molar concentration of 1×10$^{-6}$M, the scanning scope was 800-200 nm, and the optical band gap of the compound was calculated according to the following equation, $$E_{gap}^{opt} = 1240 \text{ nm}/\lambda_{onset} \quad (1)$$

Cyclic voltammetry measurement was conducted by CHI610D electrochemical analyzer with computer control using a conventional tri-electrode system with platinum electrode as a working electrode, saturated calomel electrode (SCE) as a reference electrode, and platinum wire as a counter electrode. Samples were dissolved in freshly distilled dichloromethane to a molar concentration of 1×10$^{-3}$ M. Bu$_4$NPF$_6$ (0.1 M) was applied as a supporting electrolyte. The scan rate was 50 mV/s. Using saturated calomel as reference, taking the SCE energy level to be −4.44 eV below the vacuum level, the LUMO energies for the test material can be calculated by using the following equation for energy level:

$$E_{LUMO} = -(E_{1/2}^{red1} + 4.44) \text{ eV} \quad (2)$$

Since sulfur containing heterocycle fused naphthalenetetracarboxylic acid diimide derivatives within the same class (class I: 1-8; class II: 9-11; class III: 12 and 13; class IV: 14-17; class V: 18-21) have similar UV absorption spectrum and electrochemical properties, we hereby further describe compounds 1 (wherein R$^1$ is 2-decyltetradecyl), 9 (wherein R$^1$ is 2-octyldodecyl and R$^2$ is ethyl), 12 (wherein R$^1$ is 2-decyltetradecyl and R$^3$ is H), 15 (wherein R$^1$ is 2-octyldodecyl) and 18 (wherein R$^1$ is 2-decyltetradecyl) for exemplification.

Figure 2:
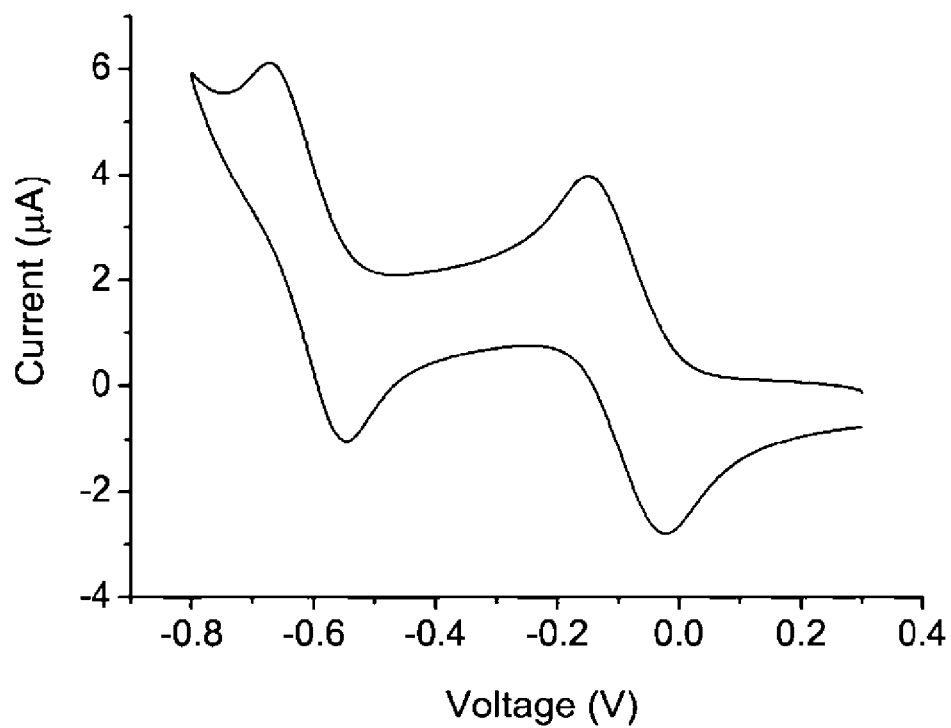
FIG. 2 shows the cyclic voltammogram for compound 1 in dichloromethane.
Figure 3:
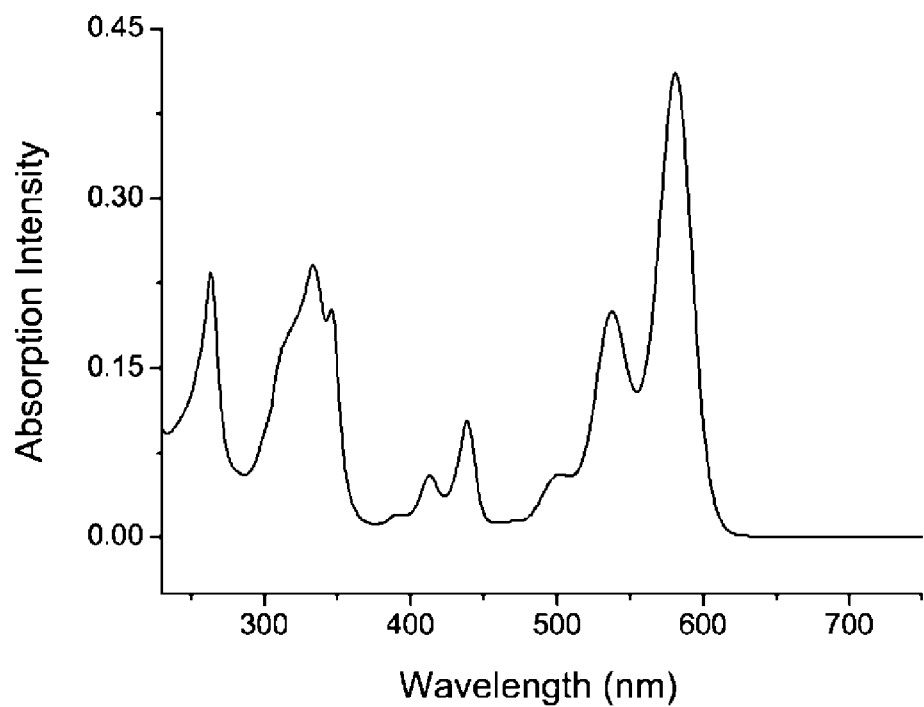
FIG. 3 shows the UV absorption spectrum for compound 9 in dichloromethane.
Figure 4:
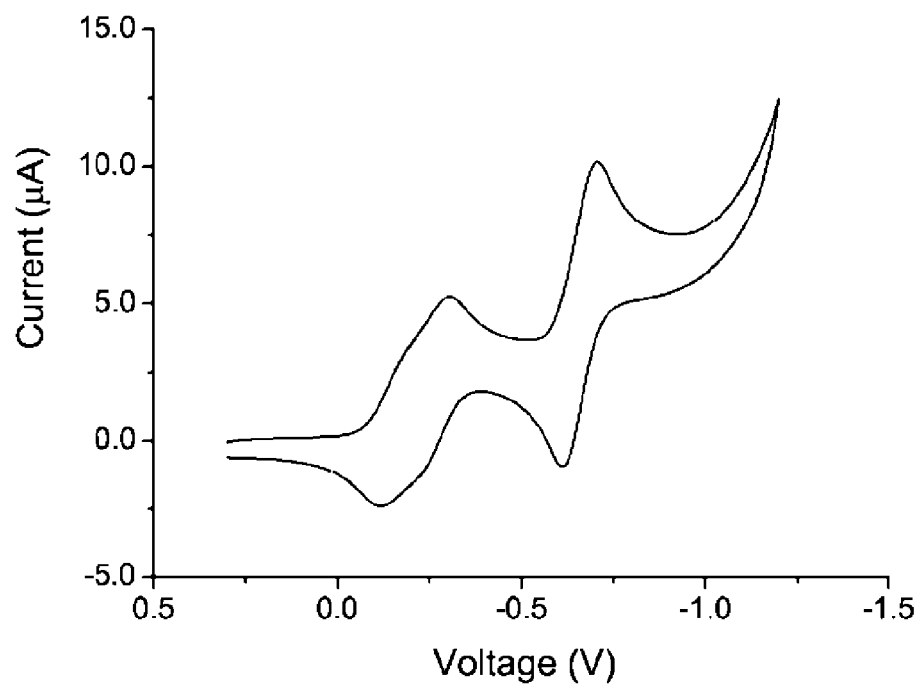
FIG. 4 shows the cyclic voltammogram for compound 9 in dichloromethane.
Figure 5:
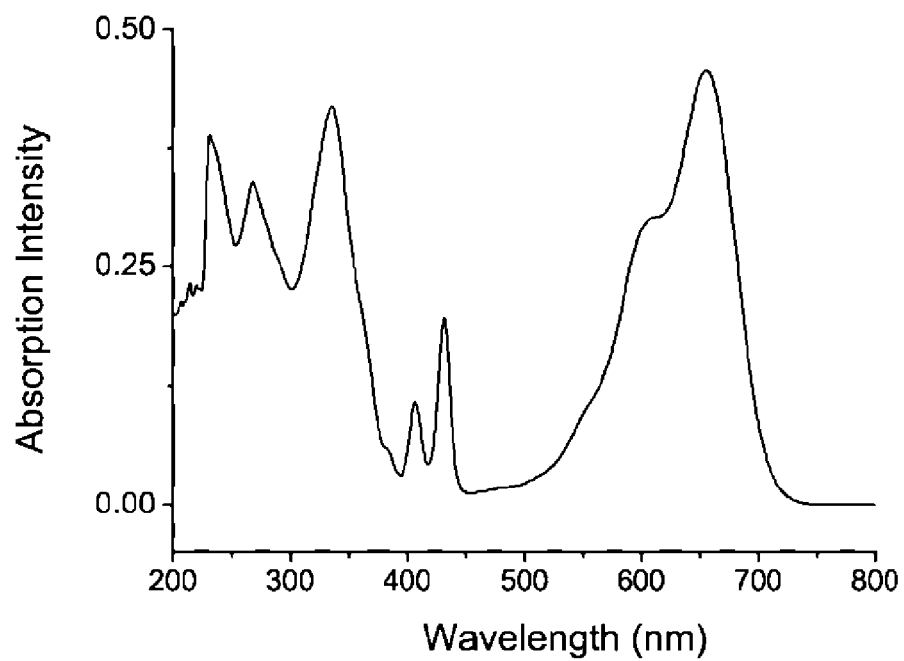
FIG. 5 shows the UV absorption spectrum for compound 12 in dichloromethane.
Figure 6:
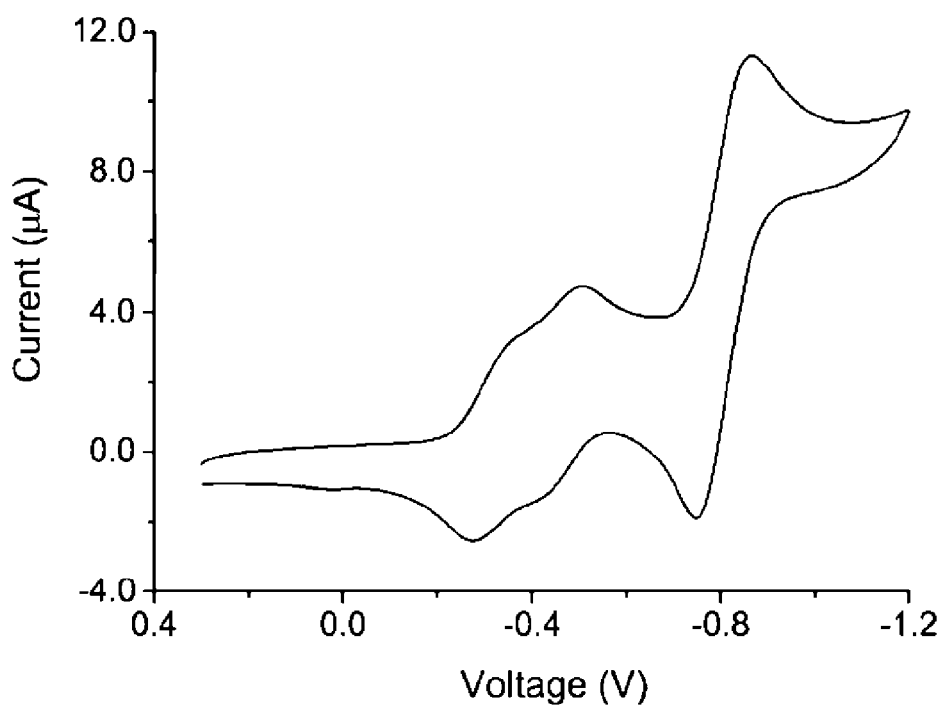
FIG. 6 shows the cyclic voltammogram for compound 12 in dichloromethane.

FIG. 1 shows the UV absorption spectrum of compound 1, whose maximum UV absorption has a peak around 573 nm, and the optical band gap is 2.1 eV. FIG. 2 shows the cyclic voltammogram of compound 1, indicating two reversible redox processes, the half-wave potentials of which are E$_{1/2}^{red1}$=−0.09 eV and E$_{1/2}^{red2}$=−0.63 eV, respectively, and the calculated LUMO energy level is −4.35 eV according to equation (2). FIG. 3 shows the UV absorption spectrum of compound 9, whose maximum end absorption has a peak around 581 nm, and the calculated optical band gap is 2.0 eV according to equation (1). FIG. 4 shows the cyclic voltammogram of compound 9, indicating two reversible redox processes, the half-wave potentials of which are E$_{1/2}^{red1}$=−0.21 eV and E$_{1/2}^{red2}$=−0.68 eV, respectively, and the calculated LUMO energy level is −4.23 eV according to equation (2). As shown in FIG. 5, the absorption spectrum of compound 12 has a maximum absorption peak at around 655 nm, and the calculated optical band gap is 1.8 eV according to equation (1). The cyclic voltammogram of compound 12 (FIG. 6) shows one irreversible redox process (with a shoulder peak) and one reversible redox process (E$_{1/2}^{red1}$=−0.81 eV), the onset reduction potential of which is E$_{red}^{onset}$=−0.23 eV, and the calculated LUMO energy level is −4.17 eV according to equation (3) as below.

$$E_{LUMO} = -(E_{red}^{onset} + 4.4) \text{ eV} \quad (3)$$

Figure 7:
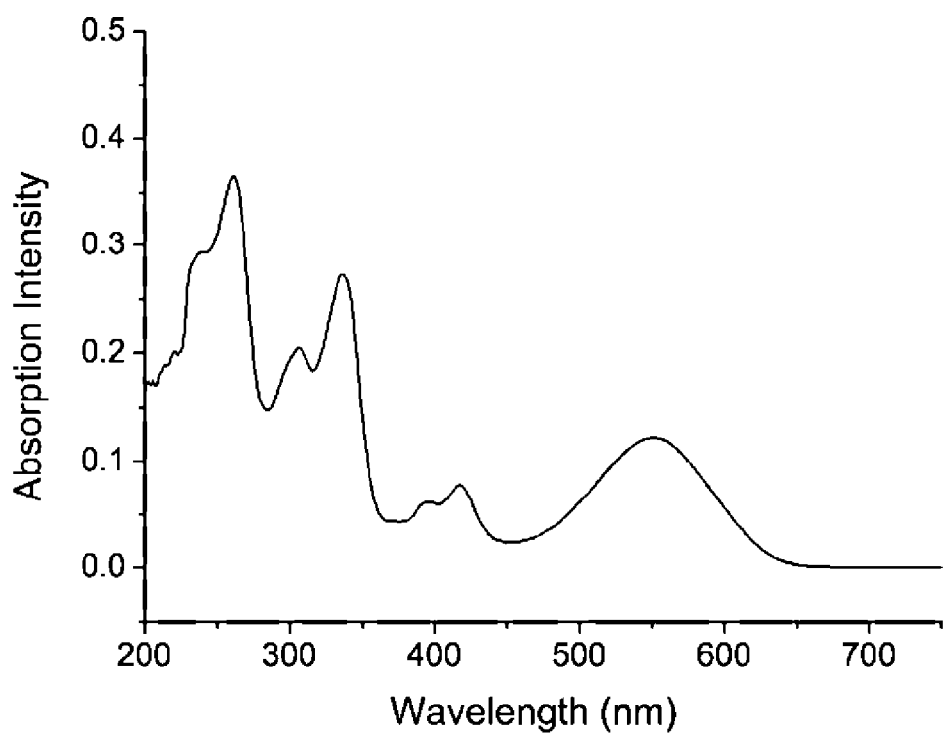
FIG. 7 shows the UV absorption spectrum for compound 15 in dichloromethane.
Figure 8:
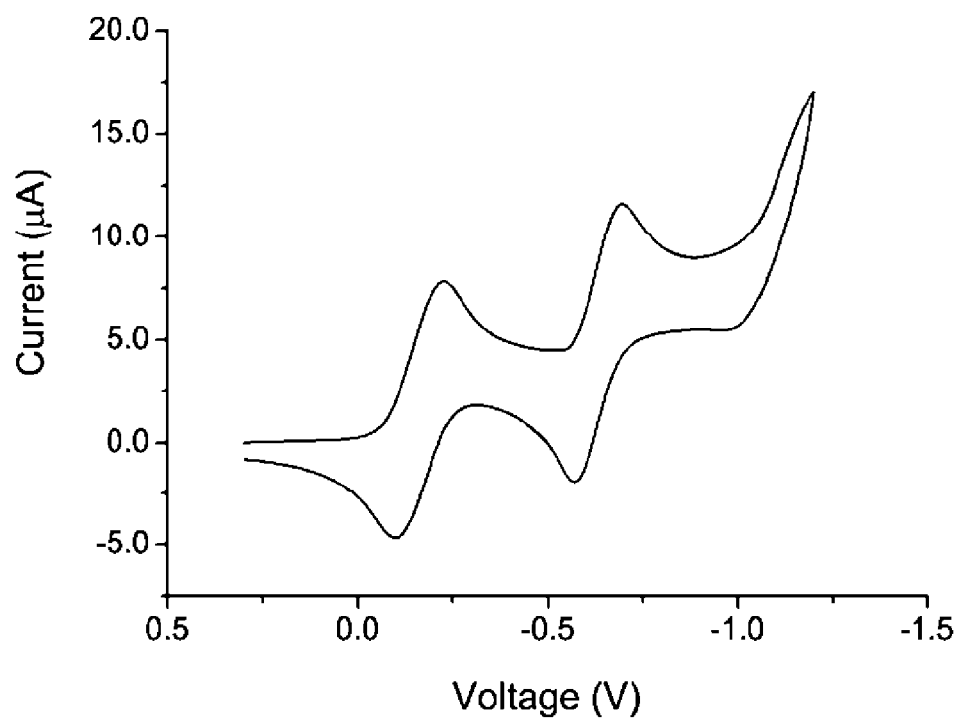
FIG. 8 shows the cyclic voltammogram for compound 15 in dichloromethane.

FIG. 7 shows the UV absorption spectrum of compound 15, whose maximum absorption has a peak around 550 nm, and the calculated optical band gap is 2.0 eV according to equation (1). FIG. 8 shows the cyclic voltammogram of compound 15, indicating two reversible redox processes, the half-wave potentials of which are $E_{1/2}^{red1}=-0.16$ eV and $E_{1/2}^{red2}=-0.64$ eV, respectively, and the calculated LUMO energy level is −4.28 eV according to equation (2).

Figure 9:
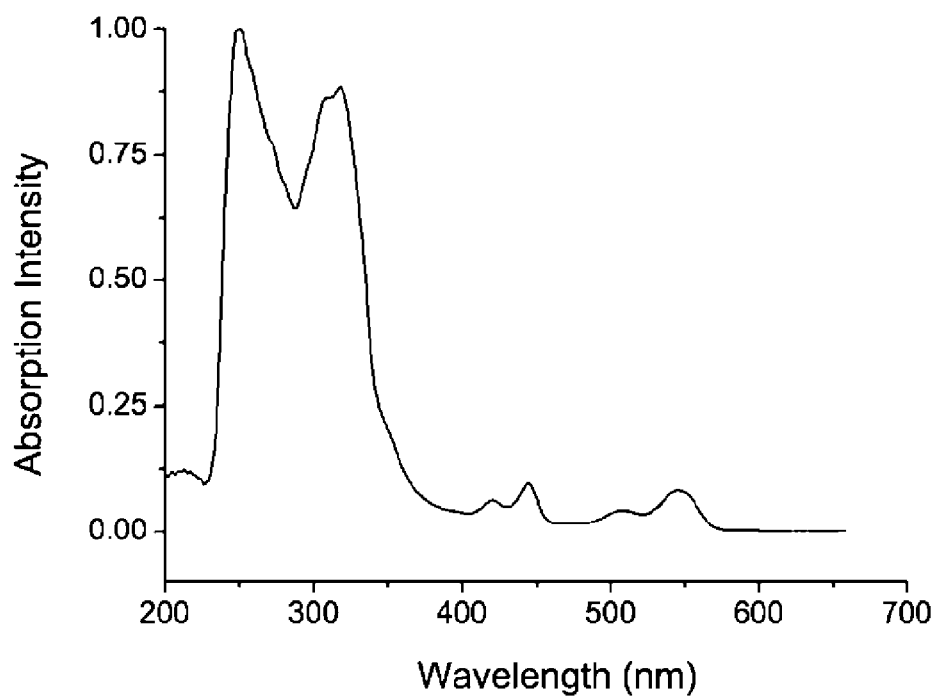
FIG. 9 shows the UV absorption spectrum for compound 18 in dichloromethane.
Figure 10:
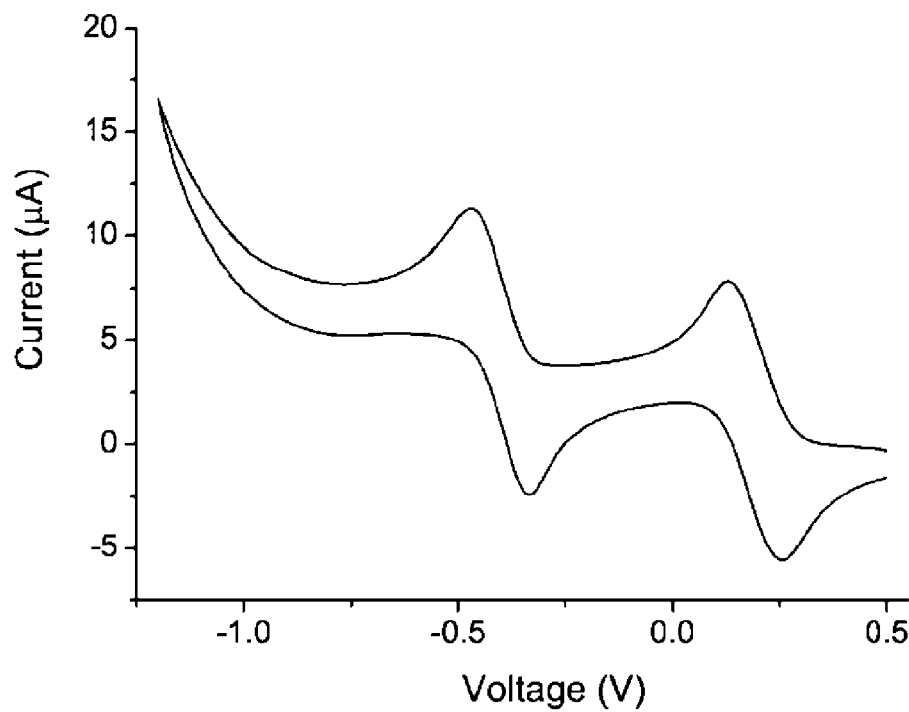
FIG. 10 shows the cyclic voltammogram for compound 18 in dichloromethane.

FIG. 9 shows the UV absorption spectrum of compound 18, whose maximum absorption has a peak in the range of 250~318 nm, and the end absorption has a peak at 545 nm with a relatively weak absorption indicating a relatively weak intramolecular charge transfer, and the calculated optical band gap is 2.2 eV according to equation (1). FIG. 10 shows the cyclic voltammogram of compound 18, indicating two reversible redox processes, the half-wave potentials of which are $E_{1/2}^{red1}=0.19$ eV and $E_{1/2}^{red2}=-0.40$ eV, respectively, and the calculated LUMO energy level is −4.63 eV according to equation (2). Class V compounds have a relatively low LUMO energy level, therefore, are a group of promising electron acceptor materials.

Figure 11:
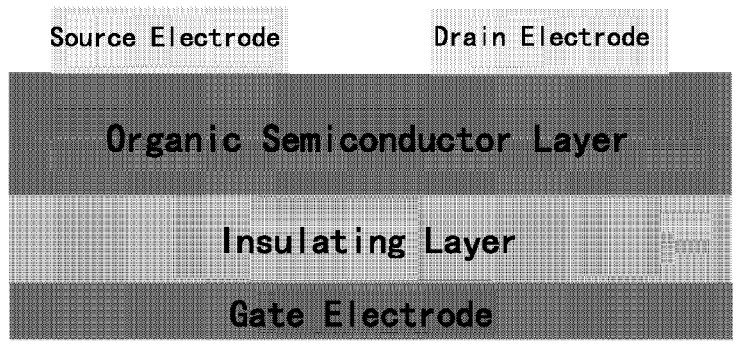
FIG. 11 is a schematic view for the structure of OTFT devices with compounds 1~5 or 7 or 9 or 10 or 15 or 18 as an organic layer.

(3) Organic thin-film transistors fabricated with compounds 1-5, 7, 9, 10, 15 and 18 as a semiconducting layer FIG. 11 shows a schematic view for the structure of organic thin-film field-effect transistors (OTFT) with aforementioned compounds as the semiconducting layer. As shown in FIG. 11, the process to fabricate the OTFT devices of the present invention was as following, 5-10 mg of compound 1-5 or 7 or 9 or 15 or 18 was dissolved into 1 ml of chloroform, a spin-coated thin film of organic semiconductor (10-80 nm in thickness) was deposited onto OTS treated $SiO_2$/Si substrate (with high doped Si substrate as a gate electrode, thickness of the thermal oxide $SiO_2$ insulating layer was 450 nm, and capacitance was 10 $nFcm^{-2}$), the film was annealed to improve the performance of the resulting devices, and a gold source drain electrode was deposited onto the organic film using mask plate to produce OTFT devices with a top-contact structure, said devices had a semiconductor channel of 50 μm in length and 3 mm in width. The electrical properties of OTFT were assayed using Keithley 4200 semiconductor analyzer at room temperature in air. The characteristic data for the electrical performance (including mobility, on/off ratio, and threshold voltage) of OTFT devices of compounds 1-5, 7, 9, 15 and 18 ($\geqq$10 devices for each compound) were listed below in Table 1.

Figure 12:
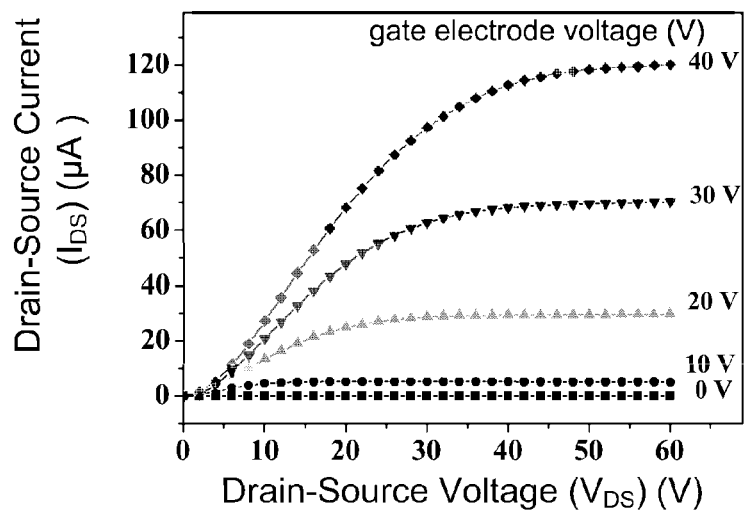
FIG. 12 shows the output curve of OTFT device based on compound 2.
Figure 13:
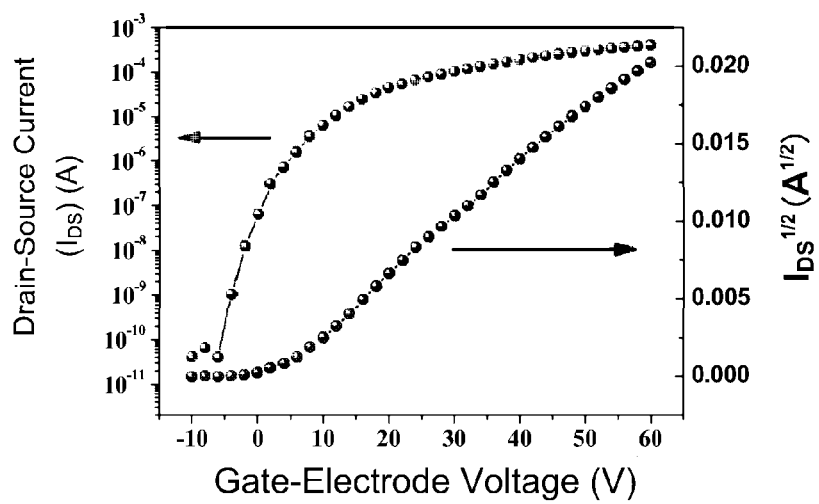
FIG. 13 shows the transfer curve of OTFT device based on compound 2 (the electron mobility is 0.36 cm$^2$/Vs, the on/off ratio is $10^7$, and the threshold voltage is 4 V)
Figure 14:
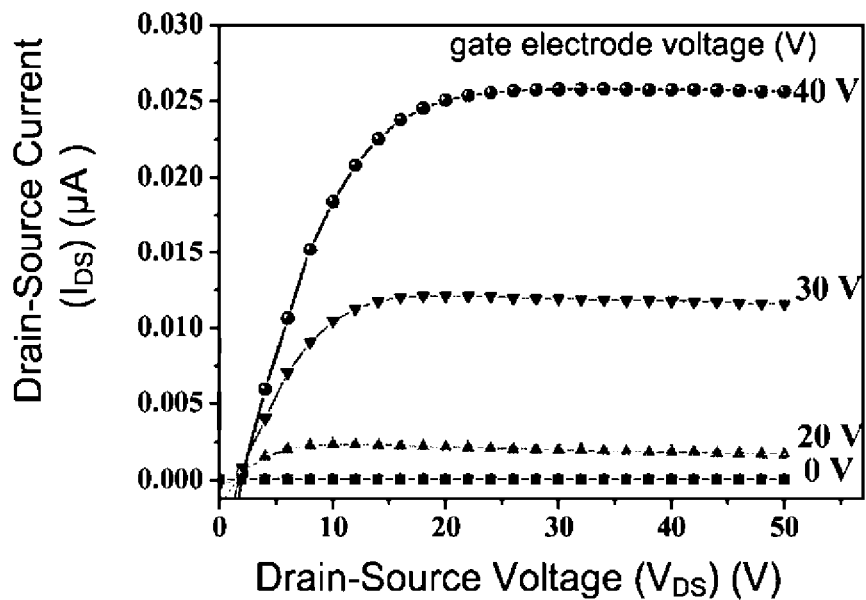
FIG. 14 shows the output curve of OTFT device based on compound 9.
Figure 15:
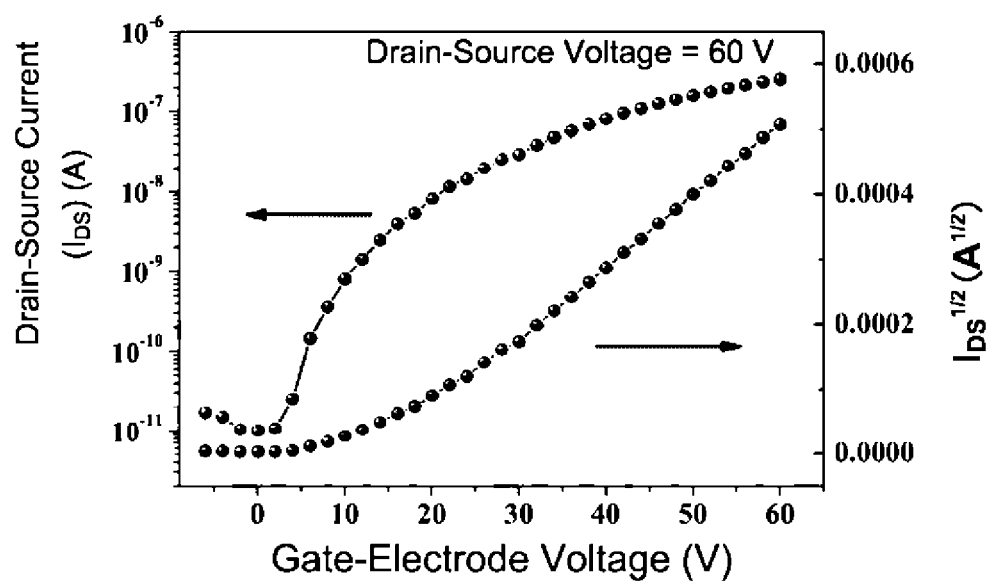
FIG. 15 shows the transfer curve of OTFT device based on compound 9 (the electron mobility is $10^{-3}$ cm$^2$/Vs, the on/off ratio is $10^4$, and the threshold voltage is 8 V)
Figure 16:
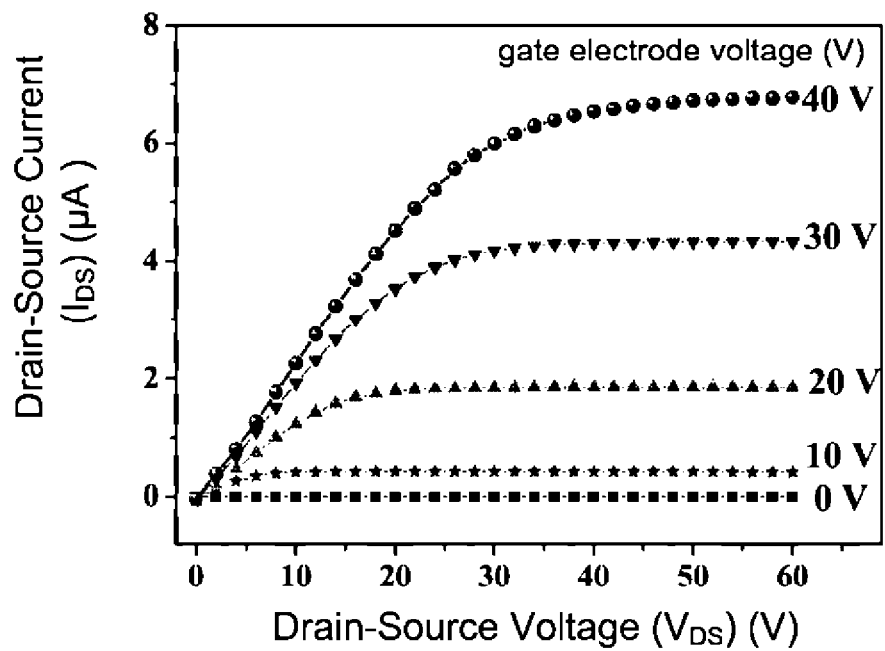
FIG. 16 shows the output curve of OTFT device based on compound 15.
Figure 17:
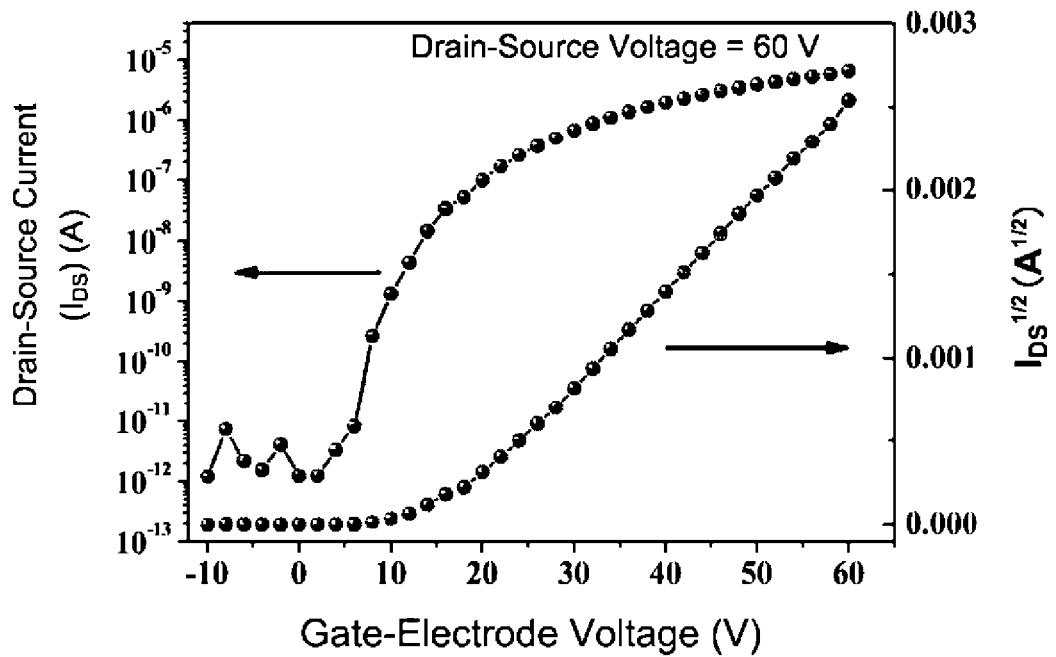
FIG. 17 shows the transfer curve of OTFT device based on compound 15 (the electron mobility is 0.016 cm$^2$/Vs, the on/off ratio is $10^6$, and the threshold voltage is 10 V)
Figure 18:
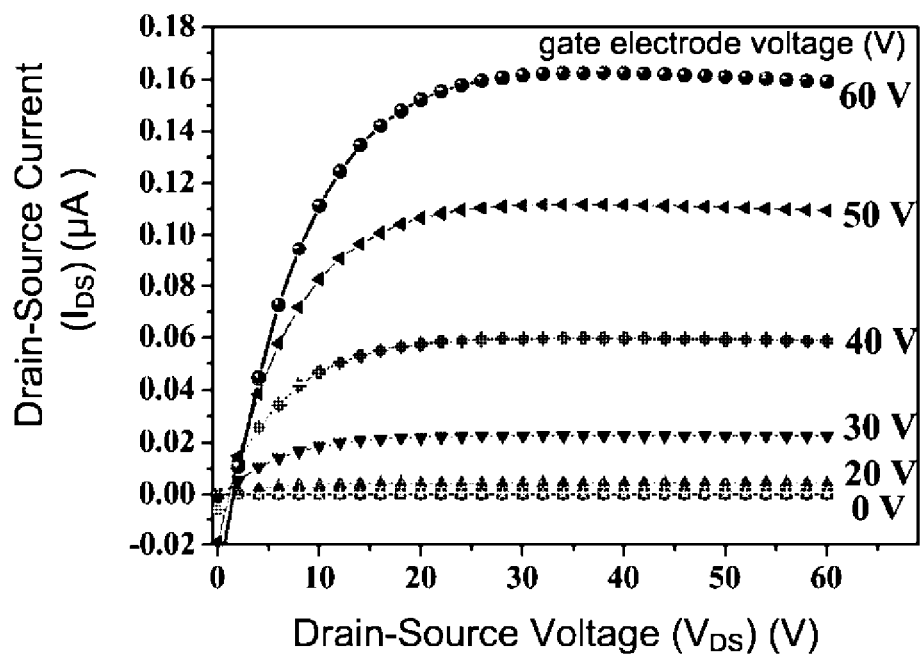
FIG. 18 shows the output curve of OTFT device based on compound 18.
Figure 19:
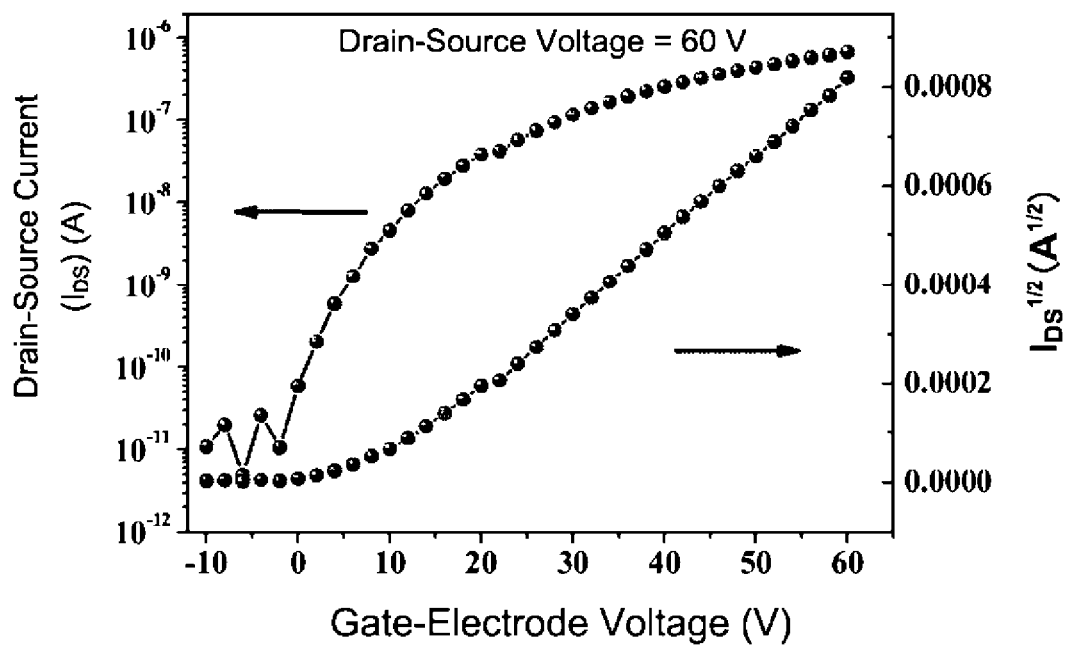
FIG. 19 shows the transfer curve of OTFT device based on compound 18 (the electron mobility is $10^{-3}$ cm$^2$/Vs, the on/off ratio is $10^5$, and the threshold voltage is 10 V).

FIGS. 12 and 13 show the output curve and transfer curve of one OTFT device based on compound 2, respectively. FIGS. 14 and 15 show the output curve and transfer curve of one OTFT device based on compound 9, respectively. FIGS. 16 and 17 show the output curve and transfer curve of an OTFT device based on compound 15, respectively. FIGS. 18 and 19 show the output curve and transfer curve of one OTFT device based on compound 18, respectively.

OTFT devices based on novel sulfur containing heterocycle fused naphthalenetetracarboxylic acid diimide derivatives were fabricated in the present invention using solution processing procedure, wherein the primary testing result of gold electrode OTFT devices based on class I compounds showed a high electron mobility of up to 0.42 $cm^2/V \cdot s$, an on/off ratio greater than $10^5$, and a threshold voltage lower than 15 V, and said devices exhibit desirable air stability and voltage operative stability.

The present invention shall not be construed as limited to the 21 disclosed exemplary compounds, there are numerous types of sulfur containing heterocycle fused naphthalenetetracarboxylic acid diimide derivatives, therefore, the scope of the invention is defined by the appended claims.

Table 1 shows the electrical performance of OTFT devices fabricated with compounds 1-5, 7, 9, 15 and 18 at various annealing temperatures, including Maximum (Average) Electron Mobilities ($\mu_e$ in $cm^2/Vs$), Current On/Off Ratios ($I_{on}/I_{off}$), and Threshold Voltages ($V_T$ in V).

TABLE 1

| | 120° C. | | | 160° C. | | | 180° C. | | |
|---|---|---|---|---|---|---|---|---|---|
| | $\mu_e$ ($cm^2/Vs$) | $I_{on}/I_{off}$ | $V_T$ (V) | $\mu_e$ ($cm^2/Vs$) | $I_{on}/I_{off}$ | $V_T$ (V) | $\mu_e$ ($cm^2/Vs$) | $I_{on}/I_{off}$ | $V_T$ (V) |
| 1 | 0.12 (0.09) | $10^5$-$10^6$ | −2-4 | 0.20 (0.15) | $10^5$-$10^6$ | −2-5 | 0.15 (0.14) | $10^5$-$10^6$ | −2-1 |
| 2 | 0.14 (0.10) | $10^5$-$10^6$ | −2-6 | 0.25 (0.20) | $10^5$-$10^6$ | 0-8 | 0.42 (0.32) | $10^5$-$10^7$ | 0-5 |
| 3 | 0.10 (0.09) | $10^5$-$10^6$ | 2-10 | 0.14 (0.13) | $10^5$-$10^6$ | 2-10 | 0.19 (0.17) | $10^5$-$10^6$ | 5-11 |
| 4 | 0.08 (0.07) | $10^5$-$10^6$ | 1-5 | 0.16 (0.15) | $10^5$-$10^6$ | 3-11 | 0.21 (0.20) | $10^5$-$10^6$ | 2-10 |
| 5 | 0.12 (0.11) | $10^5$-$10^6$ | 6-3 | 0.15 (0.14) | $10^5$-$10^6$ | 8-14 | 0.21 (0.19) | $10^6$-$10^8$ | 7-14 |
| 7 | 0.14 (0.12) | $10^6$-$10^7$ | −1-5 | 0.26 (0.24) | $10^6$-$10^7$ | −1-7 | 0.20 (0.18) | $10^6$-$10^7$ | −2-4 |
| 9 | $5 \times 10^{-4}$ ($3 \times 10^{-4}$) | $10^3$-$10^4$ | 32-45 | $1.1 \times 10^{-3}$ ($9 \times 10^{-4}$) | $10^3$-$10^4$ | 12-35 | $4 \times 10^{-3}$ ($2 \times 10^{-3}$) | $10^3$-$10^4$ | 10-16 |
| 15 | $1.5 \times 10^{-3}$ ($1.2 \times 10^{-3}$) | $10^4$-$10^5$ | 20-40 | $1.6 \times 10^{-2}$ ($1.3 \times 10^{-2}$) | $10^4$-$10^5$ | 10-35 | $7 \times 10^{-3}$ ($5 \times 10^{-3}$) | $10^4$-$10^5$ | 20-41 |
| 18 | $1.2 \times 10^{-3}$ ($6 \times 10^{-4}$) | $10^4$-$10^5$ | 2-11 | — | — | — | — | — | — |

What is claimed is:

1. A group of sulfur containing heterocycle fused naphthalenetetracarboxylic acid diimide derivatives having the following structures:

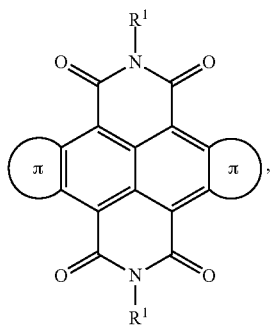

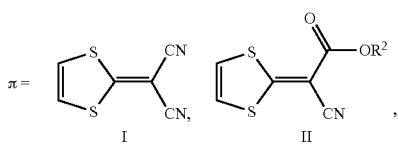

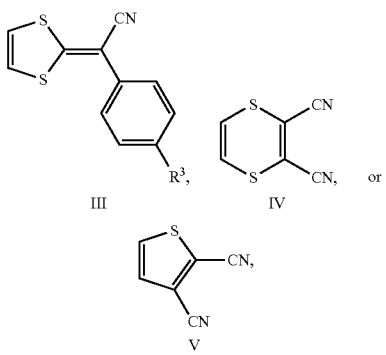

wherein, $R^1$ and $R^2$ are $C_1$~$C_{30}$ and $C_1$~$C_{12}$ n-alkyl or branched alkyl, respectively; and $R^3$ is H or halogen.

2. The group of sulfur containing heterocycle fused naphthalenetetracarboxylic acid diimide derivatives according to claim 1, which are 1,3-dithiacyclopentene fused naphthalenetetracarboxylic acid diimide derivatives having structures shown below in formula (I), (II) or (III):

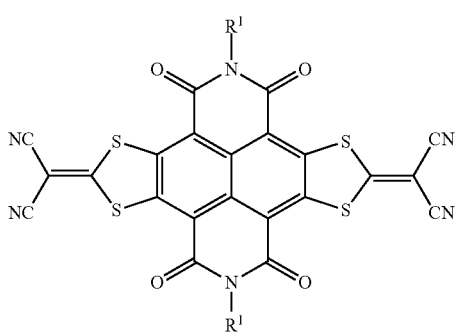

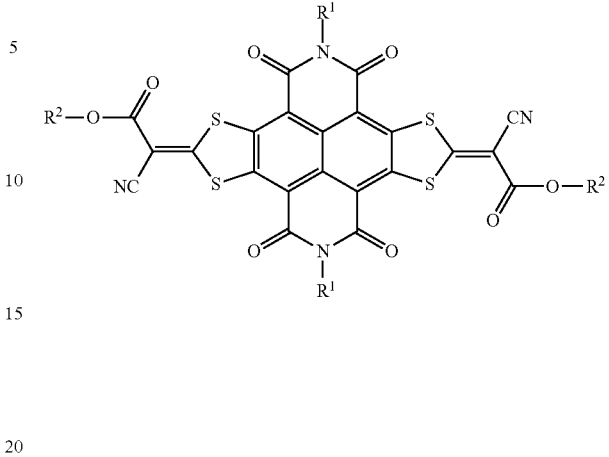

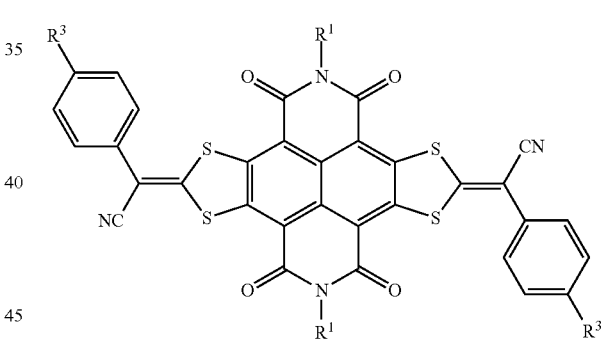

wherein $R^1$, $R^2$, and $R^3$ are as defined in claim 1.

3. The group of sulfur containing heterocycle fused naphthalenetetracarboxylic acid diimide derivatives according to claim 1, which are 1,4-dithiacyclohexadiene-2,3-dicarbonitrile fused naphthalenetetracarboxylic acid diimide derivatives having a structure shown below in formula (IV), and/or α, β-dicyanothiophene fused naphthalenetetracarboxylic acid diimide derivatives having a structure shown below in formula (V), wherein the α, β-dicyanothiophene fused naphthalenetetracarboxylic acid diimide derivative shown in formula (V) is a pair of non separable cis-trans isomers,

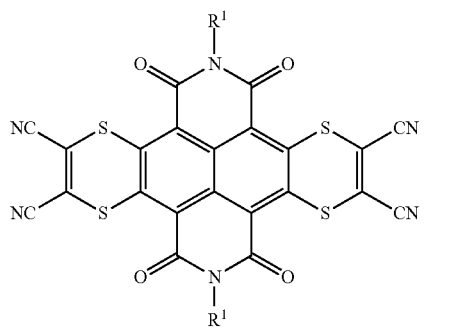

IV

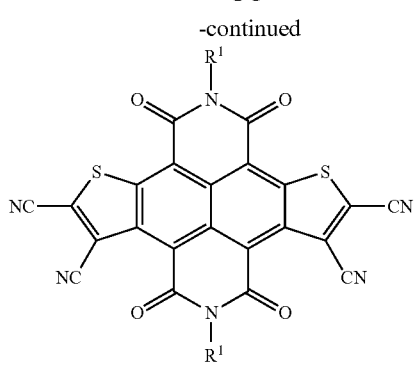

V

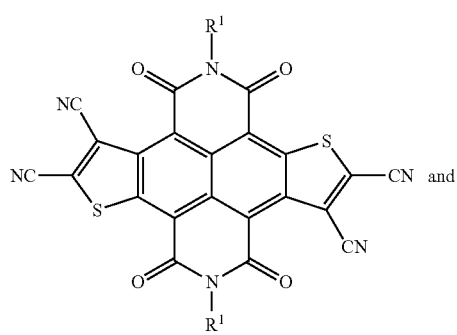

and wherein R¹ is as defined above.

4. The group of sulfur containing heterocycle fused naphthalenetetracarboxylic acid diimide derivatives according to claim 1, wherein R¹ is $C_8$~$C_{24}$ n-alkyl or branched alkyl.

5. The group of sulfur containing heterocycle fused naphthalenetetracarboxylic acid diimide derivatives according to claim 1, wherein said derivatives are selected from the groups consisting of:

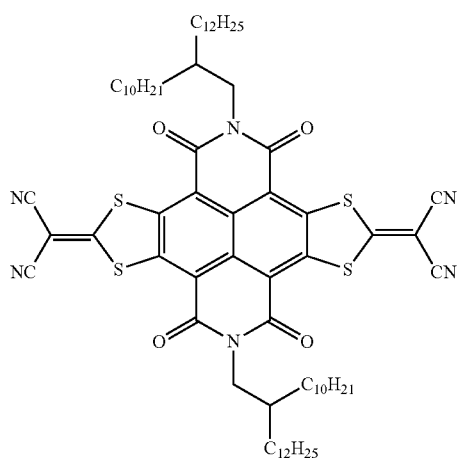

1

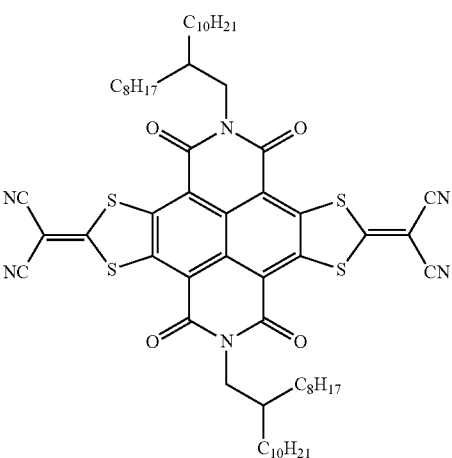

2

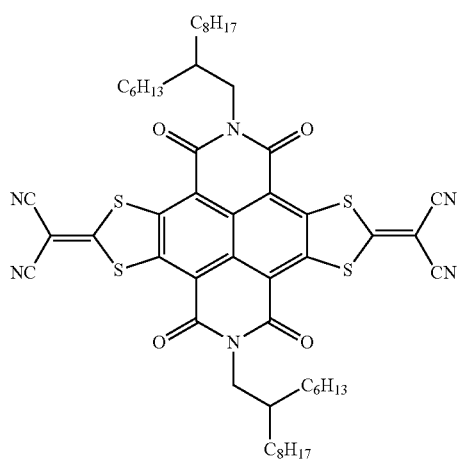

3

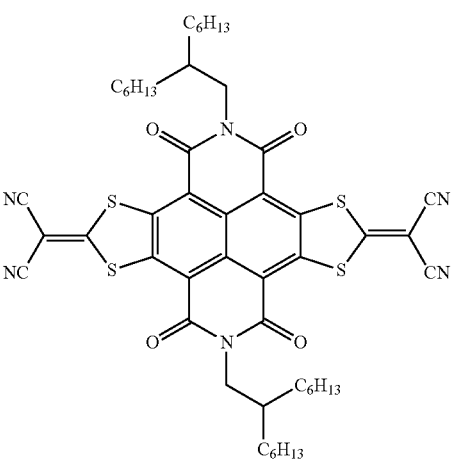

4

-continued
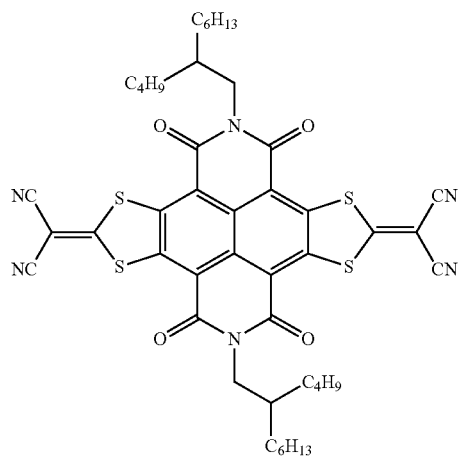
5
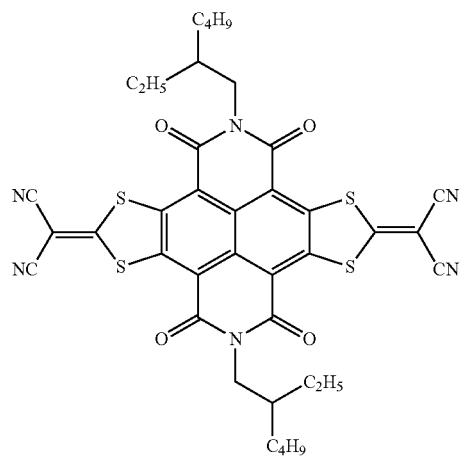
6
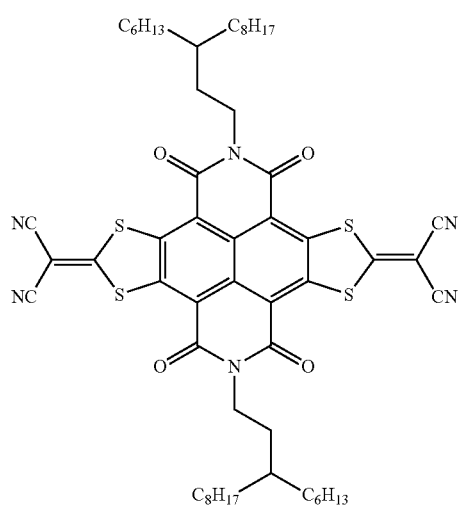
7
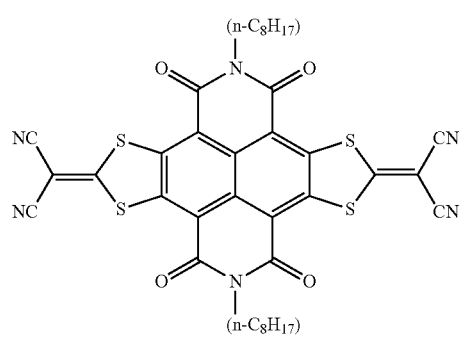
8
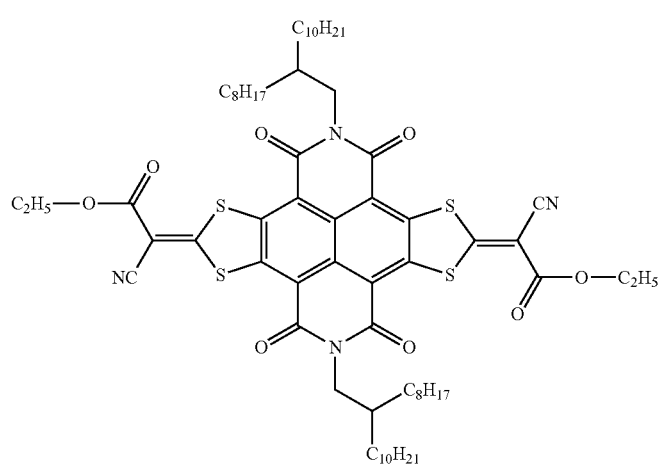
9

-continued
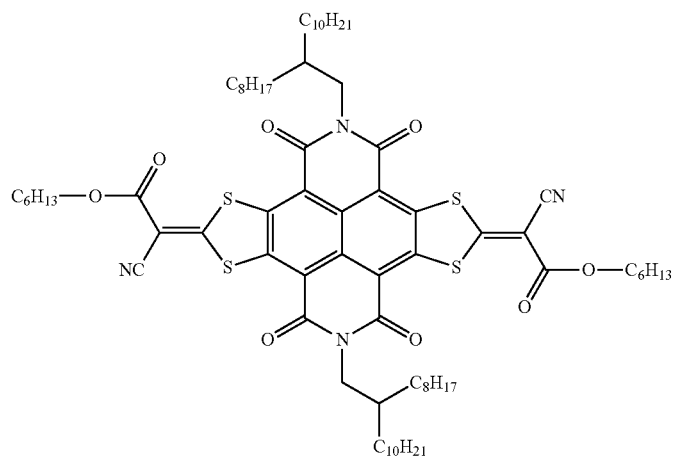
10
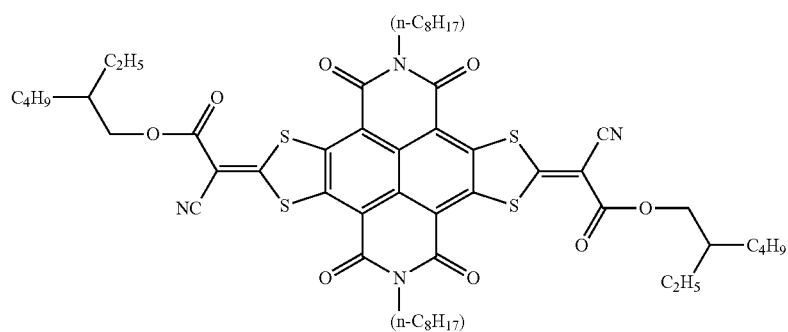
11
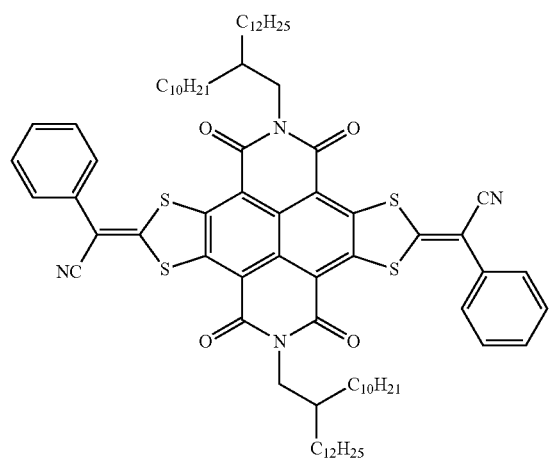
12
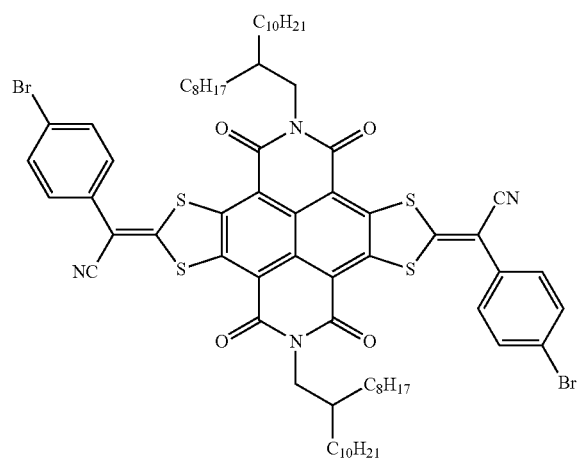
13

-continued
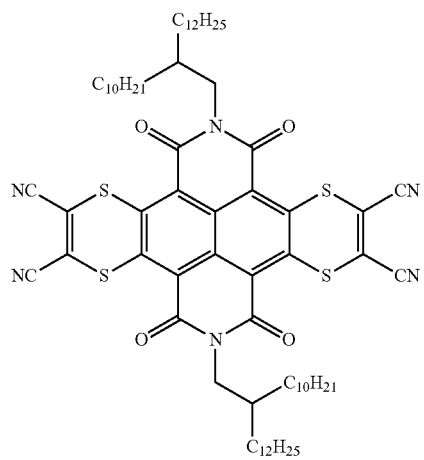
14
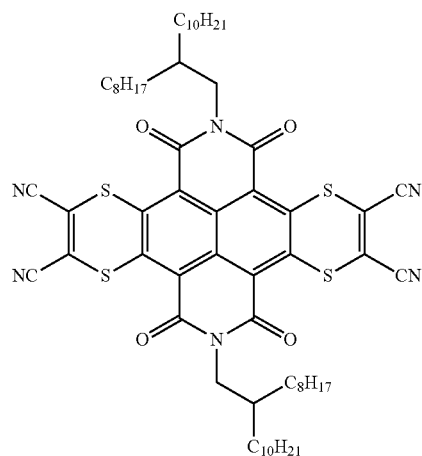
15
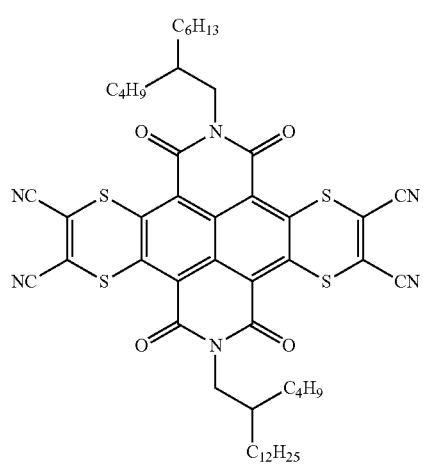
16
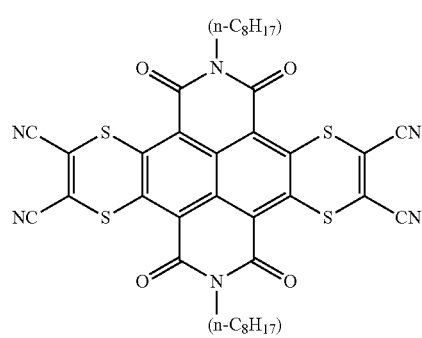
17
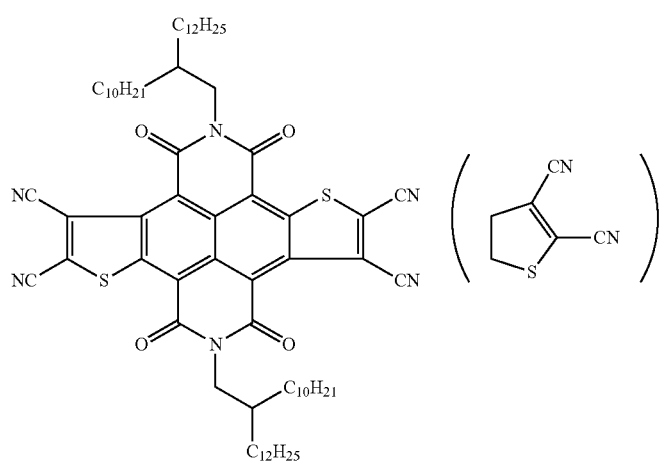
18

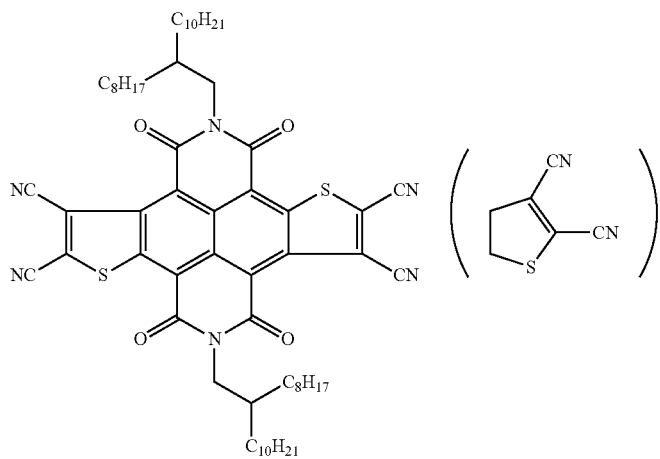

19

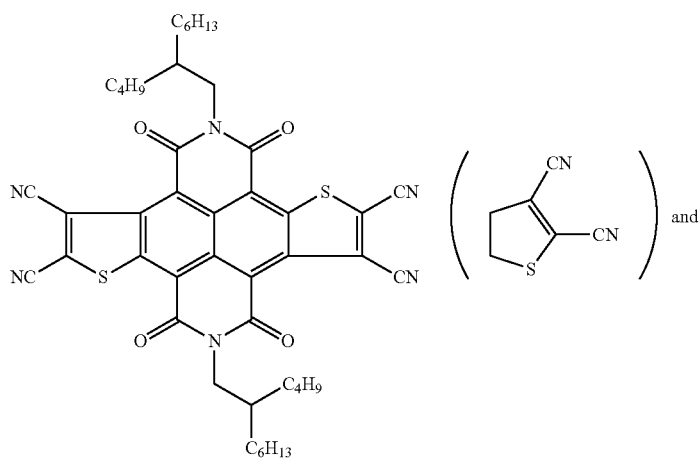

20 and

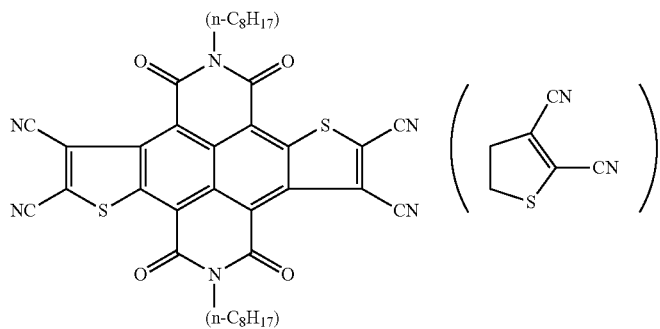

21

6. A method for the preparation of the group of sulfur containing heterocycle fused naphthalenetetracarboxylic acid diimide derivatives according to claim 1, comprising obtaining 1,3-dithiacyclopentene fused naphthalenetetracarboxylic acid diimide derivatives of general formula (I) through step (A), obtaining 1,3-dithiapentene fused naphthalenetetracarboxylic acid diimide derivatives of general formulae (II) and (III) through steps (B) and (C), obtaining 1,4-dithiacyclohexadiene-2,3-dicarbonitrile fused naphthalenetetracarboxylic acid diimide derivatives of general formula (IV) through step (D), and/or obtaining α, β-dicyanothiophene fused naphthalenetetracarboxylic acid diimide derivatives of general formula (V) through step (E), the derivatives of formula V are non separable cis-trans isomers; wherein the steps are:

(A) reacting 2,2-dicyano-ethylene-1,1-dithiol sodium with N-alkyl $R^1$ substituted 2,3,6,7-tetrabromonaphthalenetetracarboxylic acid diimide of general formula (VI) at a molar ratio of 2.5~4:1 in an organic solvent at room temperature for 0.5~2 hours followed by 40~60° C. for 0.5~1 hour, or simply reacting at room temperature for 1~6 hours;

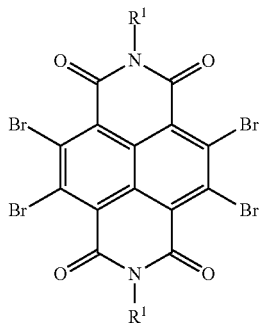

VI (B) reacting alkyl cyanoacetate $CNCH_2COOR^2$ or phenyl acetonitrile or 4-halophenyl acetonitrile with sodium hydride NaH and carbon disulfide $CS_2$ at a molar ratio of 1:2~3:1~1.5 in an organic solvent at 0~5° C. for 0.5~1 hour and at room temperature for 2~4 hours, sequentially;

(C) adding N-alkyl $R^1$ substituted 2,3,6,7-tetrabromonaphthalenetetracarboxylic acid diimide of general formula (VI) into the reaction liquid prepared through step (B) and reacting at room temperature for 0.5~2 hours, wherein the reaction mixture contains alkyl 2-cyanoacetate-ethylene-1,1-dithiol sodium or 2-phenyl acetonitrile-ethylene-1,1-dithiol sodium or 2-(4-halophenyl acetonitrile)-ethylene-1,1-dithiol sodium, and the molar ratio of N-alkyl $R^1$ substituted 2,3,6,7-tetrabromonaphthalenetetracarboxylic acid diimide to $CS_2$ in step (B) is 1:5~10;

(D) reacting N-alkyl R1 substituted 2,3,6,7-tetrabromonaphthalenetetracarboxylic acid diimide of general formula (VI) with 1,2-dicyanoethylene 1,2-dithiol sodium at a molar ratio of 1:2~3.5 in an organic solvent at room temperature for 0.5~1 hour;

(E) reacting 1,4-dithiacyclohexadiene-2,3-dicarbonitrile fused naphthalenetetracarboxylic acid diimide derivatives with hydrogen peroxide at a molar ratio of 1:50~80 in an acid at 100~120° C. for 0.5~1.5 hours;

wherein, $R^1$ and $R^2$ are $C_1$~$C_{30}$ and $C_1$~$C_{12}$ n-alkyl or branched alkyl, respectively;

and $R^3$ is H or halogen, the sulfur containing heterocycle fused naphthalenetetracarboxylic acid diimide derivatives of general formulae (I), (II), (III), (IV), (V).

7. The method according to claim 6, wherein the organic solvent is benzene, toluene, xylene, acetic acid, tetrahydrofuran, dioxane or N,N-dimethylformamide.

8. The method according to claim 6, wherein the organic solvent is tetrahydrofuran, dioxane or N,N-dimethylformamide.

9. The method according to claim 6, wherein the reactions of steps (A) to (D) are conducted under an inert gas, and the products of steps (A), (C), (D) and (E) are purified by silica gel column.

10. The method according to claim 6, wherein the acid in step (E) is acetic acid or propanoic acid.

11. An organic electronic device comprising said sulfur containing heterocycle fused naphthalenetetracarboxylic acid diimide derivatives according to claim 1.

12. An organic thin-film transistor comprising said sulfur containing heterocycle fused naphthalenetetracarboxylic acid diimide derivatives according to claim 1, wherein said sulfur containing heterocycle fused naphthalenetetracarboxylic acid diimide derivatives are used as semiconducting layers for said organic thin-film transistors.

13. An organic solar cell comprising said sulfur containing heterocycle fused naphthalenetetracarboxylic acid diimide derivatives according to claim 1, wherein said sulfur containing heterocycle fused naphthalenetetracarboxylic acid diimide derivatives are used as semiconducting layers for said organic solar cell.

* * * * *